United States Patent [19]

Sloan

[11] 4,376,767
[45] Mar. 15, 1983

[54] PYRIDYLMETHYL ESTERS OF SELECTED BIO-AFFECTING CARBOXYLIC ACIDS

[75] Inventor: Kenneth B. Sloan, Gainesville, Fla.
[73] Assignee: Merck & Co., Inc., Rahway, N.J.
[21] Appl. No.: 222,030
[22] Filed: Jan. 2, 1981
[51] Int. Cl.³ .................. A61K 31/625; C07D 499/32; C07D 501/38; C07D 213/55
[52] U.S. Cl. .................. 424/232; 260/239.1; 260/239.5; 424/241; 424/246; 424/247; 424/250; 424/251; 424/263; 424/266; 544/24; 544/35; 544/259; 544/267; 544/269; 544/270; 544/273; 544/275; 544/281; 546/342; 546/341; 546/343; 546/348
[58] Field of Search .................. 260/239.1, 239.5; 424/241, 232, 246, 247, 266, 250, 263, 251; 544/24, 259, 35, 270, 267, 281, 269, 273, 275; 546/341, 342, 343, 348

[56] References Cited

U.S. PATENT DOCUMENTS 3,883,569  5/1975  Phillips et al. .................. 260/239.5
4,001,219  1/1977  Baiocchi .......................... 260/239.5
4,105,668  8/1978  Nakanishi ........................ 260/239.1
4,219,554  8/1980  Saikawa et al. ................. 260/239.1

FOREIGN PATENT DOCUMENTS 908958 10/1962 United Kingdom ............. 260/239.5

Primary Examiner—Natalie Trousof
Assistant Examiner—Vera C. Clarke
Attorney, Agent, or Firm—Edmunde D. Riedl; Theresa Y. Cheng; Mario A. Monaco

[57] ABSTRACT

Novel pharmaceutically useful derivatives of selected known bio-affecting carboxylic acids are disclosed, said derivatives having the structural formula

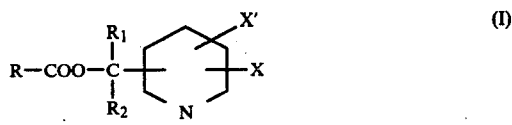

wherein $R_1$ and $R_2$, which can be the same or different, are each hydrogen, $C_1$-$C_5$ alkyl, $C_1$-$C_5$ alkoxy, $C_1$-$C_5$ alkylthio, phenyl, or substituted phenyl having one or more substituents each of which is selected from the group consisting of $C_1$-$C_5$ alkyl, $C_1$-$C_5$ alkoxy, chloro and dialkylamino wherein the alkyl portions, which can be the same or different, each have 1 to 5 carbon atoms, with the proviso that when $R_1$ is alkoxy or alkylthio, then $R_2$ cannot be alkoxy or alkylthio; X and X', which can be the same or different, are each hydrogen, $C_1$-$C_5$ alkyl, carboxy, $C_2$-$C_6$ alkoxycarbonyl, halo, $C_1$-$C_5$ alkoxy, dialkylcarbamyl wherein the alkyl portions, which can be the same or different, each have 1 to 5 carbon atoms, phenyl, or substituted phenyl the pyridyl ring is oriented such that it is attached to the

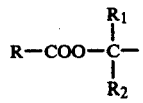

portion of the molecule via a carbon-carbon bond; and R-COO- is the acyloxy residue of a monocarboxylic acid; a steroidal monocarboxylic acid; or a cephalosporin or penicillin antibiotic.

129 Claims, No Drawings

PYRIDYLMETHYL ESTERS OF SELECTED BIO-AFFECTING CARBOXYLIC ACIDS

TECHNICAL FIELD OF THE INVENTION

The present invention relates to novel and useful biologically active derivatives of bio-affecting carboxylic acids. In particular, the present invention relates to pyridylmethyl esters of selected known bio-affecting compounds containing one or two carboxylic acid functions.

BACKGROUND OF THE PRIOR ART

It is well-known that a wide variety of compounds containing carboxylic acid functions are biologically active. For example, such structure is characteristic of non-steroidal anti-inflammatory/non-narcotic analgesic agents such as indomethacin, aspirin, naproxen and the like; cephalosporin antibiotics, e.g. cefmetazole, cefazolin, cephalexin, etc.; penicillin antibiotics such as ampicillin, amoxicillin, hetacillin and the like; as well as other compounds having diverse biological properties and the structures.

Nevertheless, it is also well-known that such prior art compounds are characterized by certain inherent disadvantages, notably serious bioavailability and physiological availability problems upon administration. Such reduced availability is attributed in part to significant ionization of the carboxylic acid functional group at physiological pH, which results in the fact that such compounds are poorly absorbed through lipid-water membrane barriers and are irritating.

Thus, a clear need exists for new derivatives of the known bio-affecting acids which will be devoid of the disadvantages inherent in those prior art compounds.

A few compounds structurally related to certain compounds of formula (I) have been reported in the literature. Thus, U.S. Pat. No. 3,897,437 to Haas et al [*Chemical Abstracts*, 83, 178848j (1975)] describes selected substituted anilinophenylacetic acid (2,3 or 4-pyridyl)methyl esters having antiinflammatory, analgesic and uv absorption properties. See also *Chemical Abstracts*, 80, 146029q (1974) describing a smaller group of pyridylalkyl (2-anilinophenyl)acetates and disclosing the same properties. Pyridylalkyl α-(4-cycloalkenyl-phenyl)propionates, useful as inflammation inhibitors and analgesics, are described in *Chemical Abstracts*, 80, 146032k (1974). *Chemical Abstracts*, 79, 115415n (1973) describes yet another group of pyridylmethyl esters, which potentiate barbiturate narcosis, some of which are also reported as having analgesic, spasmolytic and antihistaminic activity. Yet other groups of pyridylmethyl esters are reported in *Chemical Abstracts*, 79, 31888f (1973) [no utility disclosed]; *Chemical Abstracts*, 80, 82432f (1974) [no utility disclosed]; *Chemical Abstracts*, 85, 78017k (1976) [said to affect blood cholesterol and blood lipids]; *Chemical Abstracts*, 85, 192401f (1976) [said to lower serum cholesterol and blood lipids]; and U.S. Pat. No. 4,184,040 [for treatment of atherosclerosis]. See also Camble et al, *J. Chem. Soc. (C)*, 1969, 1911, which describes use of

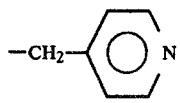

as a protecting group for amino acids in peptide synthesis. However, the compounds of the present invention are structurally distinct from the prior art compounds. Moreover, there is no suggestion in the literature that these compounds would be characterized by low pKa's, which result in enhanced stability and greater bioavailability as compared to their parent acids.

SUMMARY OF THE INVENTION

It is one object of the present invention to provide novel derivatives of selected conventional bio-affecting carboxylic acids which elicit the bio-affecting/pharmacological response characteristic of the acids from which they are derived when administered to warm-blooded animals, yet which are characterized as having good biphasic solubility and which thus are less irritating and more permeable through biological membranes, e.g., skin, gut, buccal or rectal mucosa, than are the parent compounds.

It is another object of the present invention to provide such derivatives of selected conventional bio-affecting carboxylic acids which are capable of providing a higher level of bioavailability than that possible with the parent compounds.

It is another object of the present invention to provide such derivatives of selected conventional bio-affecting carboxylic acids which have low pKa's and which are highly stable under acidic conditions (e.g. before and during absorption into the body), yet are easily cleaved in vivo as they reach systemic circulation and more basic conditions (i.e. higher pH levels) to achieve the desired biological effect.

It is yet another object of the present invention to provide such derivatives of selected conventional bio-affecting carboxylic acids which either are "soft" in nature, i.e. which are characterized by in vivo destruction to essentially non-toxic moieties, after they have achieved their desired therapeutic role [for example, the compounds derived from steroidal acids of formula (III) below], or which are "pro-drugs" designed to "cleave" upon administration to release the known and proven parent drug form at its target site or sites of activity, while the remaining "cleaved" moiety is nontoxic and is metabolized in such a manner that non-toxic metabolic by-products are produced (for example, the compounds derived from the cephalosporin and penicillin antibiotics, the non-steroidal anti-inflammatory agents, etc).

Other objects, features and advantages of the invention will be apparent to those skilled in the art from the detailed description of the invention which follows.

The foregoing objects, features and advantages are provided by the novel compounds of the formula

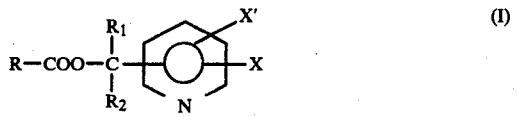

wherein $R_1$ and $R_2$, which can be the same or different, are each hydrogen, $C_1$–$C_5$ alkyl, $C_1$–$C_5$ alkoxy, $C_1$–$C_5$ alkylthio, phenyl, or substituted phenyl having one or more substituents each of which is selected from the group consisting of $C_1$–$C_5$ alkyl, $C_1$–$C_5$ alkoxy, chloro and dialkylamino wherein the alkyl portions, which can be the same or different, each have 1 to 5 carbon atoms, with the proviso that when $R_1$ is alkoxy or alkylthio, then $R_2$ cannot be alkoxy or alkylthio; X and X', which can be the same or different, are each hydrogen, $C_1$–$C_5$ alkyl, carboxy, $C_2$–$C_6$ alkoxycarbonyl, halo, $C_1$–$C_5$ alkoxy, dialkylcarbamyl wherein the alkyl portions, which can be the same or different, each have 1 to 5 carbon atoms, phenyl, or substituted phenyl having one or more substituents each of which is selected from the group consisting of $C_1$–$C_5$ alkyl, $C_1$–$C_5$ alkoxy, $C_1$–$C_6$ alkanoyl, $C_1$–$C_6$ alkanoyloxy, halo, cyano, $C_2$–$C_6$ alkoxycarbonyl, $C_1$–$C_5$ alkylthio, nitro, $C_1$–$C_5$ haloalkyl having one or more halo substituents, carboxy, $C_1$–$C_5$ alkylsulfonyl, dialkylamino wherein the alkyl portions, which can be the same or different, each have 1 to 5 carbon atoms, and dialkylcarbamyl wherein the alkyl portions, which can be the same or different, each have 1 to 5 carbon atoms; the pyridyl ring is oriented such that it is attached to the

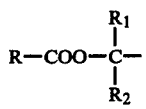

portion of the molecule via a carbon-carbon bond; and R—COO— is the acyloxy residue of:

(a) a monocarboxylic acid selected from the group consisting of indomethacin, aspirin, naproxen, sulindac, tolmetin, diflunisal, flurbiprofen, indoprofen, fenclozic acid, ketoprofen, alclofenac, bucloxic acid, cinchophen, pirprofen, oxoprozin, flufenac, flutiazin, clometacin, flufenisal, salsalate, ibuprofen, ibufenac, cinmetacin, furobufen and prodolic acid;

(b) a steroidal monocarboxylic acid having the structural formula:

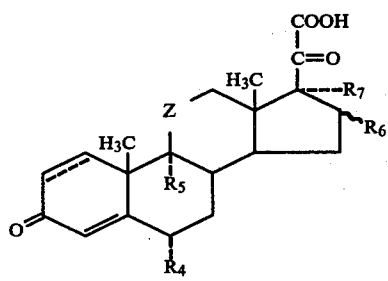

wherein $R_4$ is hydrogen, fluoro, chloro, or methyl; $R_5$ is hydrogen, fluoro or chloro; $R_6$ is hydrogen, methyl, hydroxy or —$OCOR_8$ wherein $R_8$ is $C_1$–$C_7$ straight or branched alkyl or phenyl; $R_7$ is hydrogen, hydroxy, or —$OCOR_8$ wherein $R_8$ is as defined above, with the proviso that when $R_6$ is hydroxy or —$OCOR_8$ and $R_7$ is other than hydrogen, then $R_6$ and $R_7$ are identical; or $R_6$ and $R_7$ are combined to form a divalent radical of the type

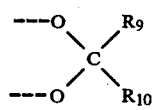

wherein $R_9$ and $R_{10}$, which can be the same or different, are each $C_1$–$C_7$ straight or branched alkyl or phenyl; Z is carbonyl or β-hydroxymethylene; the wavy line at the 16-position indicates the α or β-configuration; and the dotted line in ring A indicates that the 1,2-linkage is saturated or unsaturated;

(c) a cephalosporin antibiotic having one carboxylic acid function;

(d) a penicillin antibiotic having one carboxylic acid function; or (e) a monocarboxlic acid selected from the group consisting of γ-aminobutyric acid, captopril and valproic acid; by the novel compounds of the formula

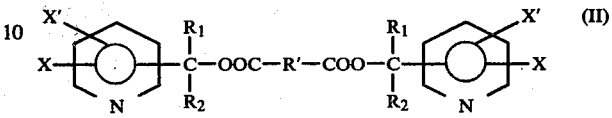

wherein the groups attached to each end of the divalent —OOC—R'—COO— residue are identical to each other; $R_1$, $R_2$, X, X' and the orientation of the pyridyl rings are as defined with respect to formula (I) above; and —OOC—R'—COO— is the di(acyloxy) residue of:

(a) a cephalosporin antibiotic having two carboxylic acid functions;

(b) a penicillin antibiotic having two carboxylic acid functions; or (c) the dicarboxylic acid, methotrexate; and by the non-toxic pharmaceutically acceptable acid addition salts, N-oxides, and quaternary ammonium salts of the compounds of formulas (I) and (II).

DETAILED DESCRIPTION OF THE INVENTION

The term "non-toxic pharmaceutically acceptable acid addition salt" as used herein generally includes the nontoxic acid addition salts of compounds of formulas (I) and (II), formed by reaction of those compounds with non-toxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic, and the like. These salts can be formed via typical methodology.

The term "quaternary ammonium salts" as used herein includes the non-toxic pharmaceutically acceptable quaternary ammonium salts of compounds of formulas (I) and (II). Typically, quaternarization of the selected compounds of formula (I) or (II) is accomplished by alkylating said compounds with an $R_3$-halide (e.g. chloride, bromide, or iodide) where $R_3$ is $C_1$–$C_{20}$ alkyl or

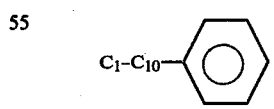

in an appropriate organic solvent, to afford the desired quaternary ammonium salts. If quaternary salts other than halides are desired, for example, 5-sulfosalicylates, $C_1$–$C_{20}$ alkylsulfonates (e.g. methanesulfonates), unsubstituted or substituted phenylsulfonates (e.g. alkyl-substituted phenylsulfonates such as p-toluenesulfonates), such can be prepared by subjecting the corresponding quaternary ammonium halides to an ion exchange method, if direct reaction is not appropriate. Exchange of the gegen ion in the quaternary salt may be accomplished using an anion exchange resin, which involves conversion of the quaternary salt to its hydroxide form and subsequent neutralization using the conjugate acid of the desired base. Alternatively, a different and generally more convenient procedure may sometimes be employed for the exchange of gegen ions in the quaternary salts. The general scheme of the exchange is illustrated below for the case of the salts derived from compounds of formula (I):

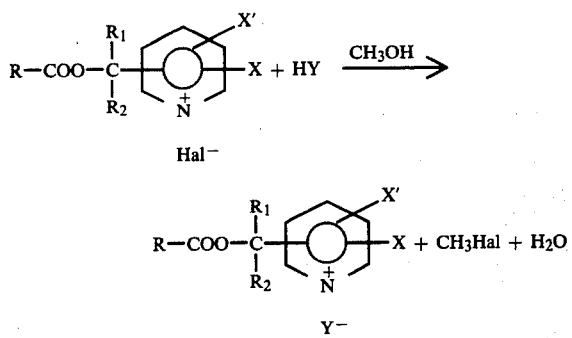

wherein R—COO—, R$_1$, R$_2$, X and X' are defined as before, Hal is I, Br or Cl and Y is Br, Cl, —CH$_3$SO$_3$, —C$_6$H$_5$SO$_3$, —CH$_3$C$_6$H$_4$SO$_3$ or other suitable acid anion. Thus, a methanolic solution of a HY acid can react with the quaternary ammonium halide to produce the methyl halide and the corresponding quaternary Y salt. This method is described in "A Convenient Method for an Ion Exchange in Quaternary Salts", J. J. Kaminski, K. W. Knutson and N. S. Bodor, *Tetrahedron*, Volume 34, pp. 2857–2859 (1978).

The term "N-oxide" as used herein includes the nontoxic pharmaceutically acceptable N-oxides of compounds of formulas (I) and (II). The N-oxides can be prepared by oxidation of the selected compound of formulas (I) or (II) with a suitable oxidizing agent, e.g. m-chloroperbenzoic acid or hydrogen peroxide, in an appropriate inert solvent such as dichloromethane, benzene or chloroform, at a temperature of from 0° C. to room temperature, for 1 to 8 hours, followed by isolation in the usual manner. Alternatively, the N-oxide can be formed at an earlier stage in the synthetic scheme, as will be more apparent from the process discussion hereinbelow.

The term "acyloxy residue" as used herein with respect to any one of the selected bio-affecting monocarboxylic acids named in conjunction with formula (I) above is intended to represent that part of the bio-affecting parent compound which remains after removal of the hydrogen atom from the —COOH portion of the molecule. Similarly, the term "di(acyloxy) residue" as used herein with respect to any one of the selected bio-affecting dicarboxylic acids named in conjunction with formula (II) above is intended to represent that part of the bio-affecting parent compound which remains after removal of the hydrogen atom from each of the —COOH portions of the molecule.

With respect to the radicals encompassed by the structural variables in formulas (I) and (II) and throughout this specification, the following definitions are applicable.

The alkyl radicals include methyl, ethyl, propyl, butyl and pentyl and the branched-chain isomers thereof, as well as their straight and branched-chain higher homologues in the instances wherein "alkyl" can contain more than 5 carbon atoms. Additionally, the alkoxy, alkylthio, dialkylamino, alkoxycarbonyl, dialkylcarbamyl, alkanoyl, alkanoyloxy and alkylsulfonyl radicals are of the type

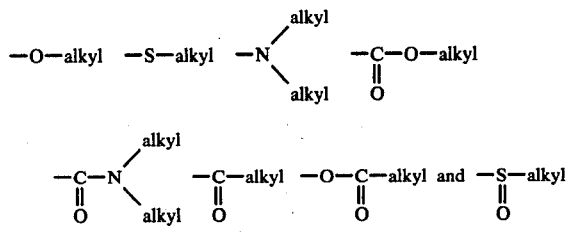

respectively, wherein the alkyl group in each instance contains 1 to 5 carbon atoms and can be straight or branched-chain. Also, the term "halo" is entented to encompass any suitable member of the halogen series, e.g. chloro, bromo or iodo. Similarly, the expression "haloalkyl having one or more halo substituents" encompasses straight or branched alkyl radicals bearing one or more of the aforementioned halo groups as substitutents, e.g. trifluoromethyl, chloromethyl and the like.

The present inventor has found that selected compounds which contain one or two carboxylic acid functional groups and which are biologically active can be advantageously derivatized according to the present invention to afford the corresponding compounds of formulas (I) and (II) and their pharmaceutically acceptable acid addition salts, quaternary ammonium salts, and N-oxides, which derivatives exhibit the advantages indicated hereinabove as to improved bioavailability, etc. as compared to their parent acids. The compounds of formulas (I) and (II), their salts and N-oxides are particularly desirable because they possess low pka's, which result in their enhanced stability and greater bioavailability as compared to their parent acids. Thus, the compounds of the invention are stable when administered orally and subjected to the acidic contents of the stomach, or when applied topically where the skin has a pH of about 4.6. However, when they are finally absorbed into the systemic circulation (pH 7.4), they are readily cleaved to release the pharmacologically active species.

As will be clear from the discussion and examples which follow, in some cases the parent carboxylic acids contain reactive moieties (in addition to the carboxy group) which must be protected during the reaction which forms the pyridylmethyl esters. The protecting groups are then subsequently removed to afford the desired compounds of the invention.

One important group of bio-affecting carboxylic acids which can be derivatized according to the present invention consists of the non-steroidal anti-inflammatory/non-narcotic analgesic/anti-pyretic agents selected from the group consisting of indomethacin, aspirin, naproxen, sulindac, tolmetin, diflunisal, flurbiprofen, indoprofen, fenclozic acid, ketoprofen, alclofenac, bucloxic acid, cinchophen, cinmetacin, furobufen, prodolic acid, pirprofen, oxoprozin, fluprofen, flutiazin, ibuprofen, ibufenac, clometacin, flufenisal and salsalate. Some members of this group are known to be useful for other purposes as well, e.g. in the treatment of rheumatic fever and other kinds of arthritis.

Another significant group of bio-affecting carboxylic acids which can be derivatized to form the compounds of the present invention comprises the cephalosporin antibiotics. Generally speaking, members of this group of antibacterial agents have the skeletal structure

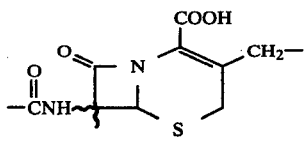

the free valences being satisfied by a variety of different substituents which do not adversely affect the antibiotic/antibacterial properties of the resultant compounds. Suitable substitutents are known to those skilled in the art and also will be readily apparent from the known structures of the particular cephalosporins named below. Especially significant members of this group include cefmetazole, cefazolin and cephalexin. Examples of other parent carboxylic acids in this category include cefoxitin, cephacetrile, cephaloglycin, cephaloridine, cephalosporin C, cephalotin, cephamycin A, cephamycin B, cephamycin C, cephapirin and cephradine. Still other suitable parent acids will be apparent to those skilled in the art.

Yet another group of bio-affecting carboxylic acids which can be derivatized to form the compounds of the present invention comprises the penicillin antibiotics. Generally, members of this group of antibacterial or antimicrobial agents are characterized by the skeletal structure

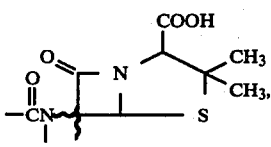

the free valences being satisfied by various substitutents which do not adversely effect the antibiotic properties of the resultant compounds. Appropriate substituents are known to those skilled in the art and will also be apparent from the known structures of the particular penicillins named below. Particularly noteworthy members of this group of parent acids include ampicillin, amoxicillin and hetacillin. Other significant parent acids in this category include carfecillin, carindacillin, carbenicillin, amylpenicillin, azidocillin, benzylpenicillinic acid, clometacillin, cloxacillin, cyclacillin, methicillin, nafcillin, 2-pentenylpenicillin, penicillin BT, penicillin N, penicillin O, penicillin S, penicillin V (phenoxymethyl penicillin), chlorbutin penicillin, dicloxacillin, diphenicillin, heptylpenicillin and metampicillin. However, this listing is not intended to be exhaustive and other acids in this category will be apparent to those skilled in the art.

Other parent acids which can be derivatized according to the present invention include GABA ($\gamma$-aminobutyric acid), an anticonvulsant; captopril, an antihypertensive; valproic acid, an anticonvulsant and antiepileptic; and methotrexate, an antineoplastic and antimetabolite.

Another group of parent acids, useful as antiinflammatory agents when esterified at the 21-position, which can be derivatized according to the present invention are the steroids of the structural formula

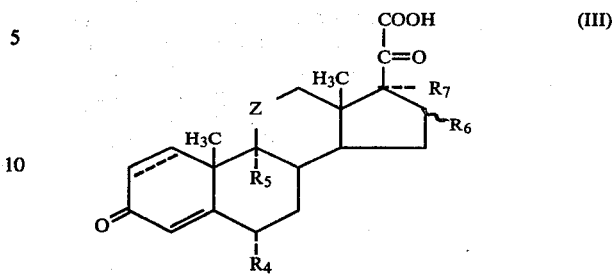

wherein $R_4$ is hydrogen, fluoro, chloro or methyl; $R_5$ is hydrogen, fluoro or chloro; $R_6$ is hydrogen, methyl, hydroxy or —$OCOR_8$ wherein $R_8$ is $C_1$–$C_7$ straight or branched alkyl or phenyl; $R_7$ is hydrogen, hydroxy or —$OCOR_8$ wherein $R_8$ is as defined above, with the proviso that when $R_6$ is hydroxy or —$OCOR_8$ and $R_7$ is other than hydrogen, then $R_6$ and $R_7$ are identical; or $R_6$ and $R_7$ are combined to form a divalent radical of the type

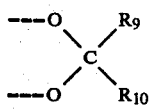

wherein $R_9$ and $R_{10}$, which can be the same or different, are each $C_1$–$C_7$ straight or branched alkyl or phenyl; Z is carbonyl or $\beta$-hydroxymethylene; the wavy line at the 16-position indicates the $\alpha$ or $\beta$-configuration; and the dotted line in ring A indicates that the 1,2-linkage is saturated or unsaturated. A particularly preferred group of carboxylic acids of formula (III) consists of the compounds wherein the structural variables represented by $R_4$, $R_5$, $R_6$, $R_7$ and Z and the dotted and wavy lines are identical to those of a known anti-inflammatory steroid selected from the group consisting of hydrocortisone, betamethasone, dexamethasone, prednisolone, triamcinolone, fluocortolone, cortisone, fludrocortisone, chloroprednisone, flumethasone, fluprednisolone, meprednisone, methyl prednisolone, paramethasone, prednisone, flurandrenolone acetonide, amcinafal, amcinafide, clocortolone, desonide, desoximetasone, difluprednate, flunisolide, fluocinolone acetonide, triamcinolone acetonide, betamethasone 17-benzoate and betamethasone 17-valerate. Another preferred group of compounds of formula (III) consists of the compounds wherein the structural variables represented by $R_4$, $R_5$, $R_6$, Z and the dotted and wavy lines are identical to those of a known anti-inflammatory steroid selected from the group consisting of hydrocortisone, cortisone, fludrocortisone, betamethasone, chloroprednisone, dexamethasone, flumethasone, fluprednisolone, meprednisone, methyl prednisolone, paramethasone and prednisolone, and $R_7$ is —$OCOR_8$ wherein $R_8$ is as hereinbefore defined, most especially when $R_8$ is $CH_3$, $C_2H_5$, $C_3H_7$ or phenyl. Yet another preferred group of parent acids of formula (III) consists the compounds wherein the structural variables represented by $R_4$, $R_5$, Z and the wavy and dotted lines are identical to those of triamcinolone, and $R_6$ and $R_7$ are identical —$OCOR_8$ groupings wherein $R_8$ is as hereinbefore defined, most especially when $R_8$ is $CH_3$, $C_2H_5$, $C_3H_7$ or phenyl. Particularly preferred parent acids encompassed by formula (III) include 6 α-fluoro-11β-hydroxy-16α-methyl-3,20-dioxopregna-1,4-dien-21-oic acid; 9α-fluoro-11β,17α-dihydroxy-16β-methyl-3,20-dioxopregna-1,4-dien-21-oic acid; 9α-fluoro-11β,17α-dihydroxy-16α-methyl-3,20-dioxopregna-1,4-dien-21-oic acid; 11β,17α-dihydroxy-3,20-dioxopregn-4-en-21-oic acid; 9α-fluoro-11β,16α,17α-trihydroxy-3,20-dioxopregna-1,4-dien-21-oic acid; and 11β,17α-dihydroxy-3,20-dioxopregna-1,4-dien-21-oic acid; as well as the corresponding 17-esters of the specific 17-hydroxy compounds just named, most especially the 17-propionates, butyrates and benzoates thereof.

While all of the compounds encompassed by formulas (I) and (II) and their acid addition and quaternary ammonium salts and N-oxides essentially satisfy the objectives of the present invention, preferred compounds include those derived from indomethacin, aspirin, naproxen, sulindac, diflunisal, cefmetazole, cefazolin, cephalexin, ampicillin, amoxicillin, penicillin V, hetacillin, GABA, captopril, methotrexate, valproic acid, 6α-fluoro-11β-hydroxy-16α-methyl-3,20-dioxopregna-1,4-dien-21-oic acid, 9α-fluoro-11β,17α-dihydroxy-16β-methyl-3,20-dioxopregna-1,4-dien-21-oic acid, 9α-fluoro-11β,17α-dihydroxy-16α-methyl-3,20-dioxopregna-1,4-dien-21-oic acid, 11β,17α-dihydroxy-3,20-dioxopregn-4-en-21-oic acid, 9α-fluoro-11β,17α,17α-trihydroxy-3,20-dioxopregna-1,4-dien-21-oic acid, and 11β,17α-dihydroxy-3,20-dioxopregna-1,4-dien-21-oic acid. Particularly preferred compounds of the invention include those wherein R—COO— or —OOC—R'—COO— is derived from one of the specific bio-affecting acids named in the preceding sentence, and $R_1$ and $R_2$ are each hydrogen or one of $R_1$ and $R_2$ is hydrogen and the other of $R_1$ and $R_2$ is methyl or phenyl, especially when X and X' are each hydrogen, or one of X and X' is hydrogen and the other is methyl, or both X and X' are methyl, and most especially when R—COO—C($R_1$)($R_2$)— or —($R_2$)($R_1$)C—OOC—R'—COO—C($R_1$)($R_2$)— is located ortho or para to the pyridyl nitrogen atom. Especially preferred species are described in the Examples hereinafter.

The compounds of the present invention can be prepared by a variety of synthetic routes, the method of choice depending upon the particular end product desired. One generally applicable process comprises reacting an alcohol of the formula

 (IV)

wherein the structural variables are defined as hereinabove, with the parent acid or the corresponding acid chloride of the desired compound of formula (I) or (II), followed by, if desired, forming the corresponding salt or N-oxide as described hereinabove. Thus, the compounds of formula (I) are prepared by reacting the selected alcohol of formula (IV) with an acid of the formula

R—COOH (V)

wherein R—COO— is defined as before, or with the corresponding acid chloride of the formula R—COCl (VI).

Similarly, the compounds of formula (II) are prepared by reacting the selected alcohol of formula (IV) with a dicarboxylic acid of the formula

HOOC—R'—COOH (VII)

wherein —OOC—R'—COO— is defined as before, or with the corresponding acid chloride, i.e.

ClOC—R'—COCl (VIII).

Obviously, in the latter case, two equivalents of alcohol will be reacted with each equivalent of diacid or di(acid chloride). Also, when an acid starting material is employed, i.e., a compound of formula (V) or (VII), then the reaction is conducted in the presence of a suitable dehydrating agent, for example dicyclohexylcarbodiimide, dimethylformamide dimethyl acetal or the like. The reaction utilizing an acid starting material is conveniently conducted in an inert solvent, such as dichloromethane, dioxane, acetone or the like, at a temperature of from 0° to 60° C., for from 1 to 16 hours. When dicyclohexylcarbodiimide is used, the equivalent of a weak base such as pyridine or a catalytic amount of an acid such as zinc chloride may be used to promote the reaction. Also in the case of using DCCD, the urea that precipitates is removed by filtration, the filtrate is concentrated and the concentrate is purified by conventional means to afford the desired compound of the invention. When the reaction utilizes an acid chloride starting material, the process can be conveniently carried out by reacting the compound of formula (IV) with the desired acid chloride in an inert solvent such as benzene, dichloromethane, dimethylformamide, acetone, tetrahydrofuran, dioxane or the like, at from room temperature to reflux (after the reaction mixture has been cooled during the mixing step), for from one to eight hours, in the presence of an acid scavenger such as an alkali metal carbonate, or an organic base such as triethylamine, or even with an additional quantity of the hydroxymethyl substituted pyridine reactant of formula (IV) [i.e. a second equivalent of the formula (IV) reactant in the case of preparing compounds of formula (I), or a third and fourth equivalent of the formula (IV) reactant in the case of preparing compounds of formula (II)]. The product may be conveniently isolated by removing the salts by filtration, evaporating the filtrate and purifying the residue by chromatography, distillation, crystallization or other suitable procedure, or by converting the pyridylmethyl ester to its acid addition salt and crystallizing the salt from a mixed solvent system such as dichloromethane/tetrahydrofuran.

The acid chlorides of formulas (VI) and (VIII) which can be used in the above method are prepared from the corresponding acids by known means, e.g. by treatment of the acid with thionyl chloride.

While the basic method described above can be used to prepare any of the compounds of the invention, certain conditions and/or modifications therein are made in specific instances. Thus, for example, the basic synthetic method described above is modified in the instances in which the desired product of formula (I) or (II) contains free amino (primary or secondary), hydroxy or thiol groupings which, if present in the acid or acid chloride starting material, would undergo undesired side reaction and/or would interfere with the desired course of the above-described acylation. In such cases, the alcohol of formula (IV) is reacted with an acid of the formula

 (IX)

or

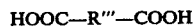 (X)

wherein R''—COO— is the (—OH and/or amino and/or —SH protected)acyloxy residue of a bio-affecting (—OH and/or amino and/or —SH containing)monocarboxylic acid, and —OOC—R'''—COO— is the (—OH and/or amino and/or —SH protected)-di(acyloxy) residue of a bioaffecting (—OH and/or amino and —SH containing)dicarboxylic acid. The hydroxy, amino and thiol functions in the parent acids of formulas (V) and (VII), respectively, are converted to their protected counterparts in formulas (IX) and (X) by known methods, e.g. those known in the art of peptide synthesis. An especially desirable route to the protected acids of formulas (IX) and (X) comprises reacting the appropriate carboxylic acid of formula (V) or (VII) having other reactive functional groups such as —OH and —NH₂ with an excess of vinyl chloroformate

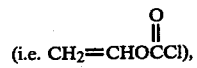

while maintaining the pH at between 7 and 8 (for example, using a pH stat), to give the completely protected acid wherein, for example, the H of the —OH group and one H of the —NH₂ group are replaced with vinyloxycarbonyl (—COOCH=CH₂) units. [See Olofson et al, *Tetrahedron Letters*, 18, 1571–1574 (1977)]. When protected hydroxy and/or thiol groups as well as amino groups are present, the resultant protected acid can be converted to the corresponding intermediate containing free —OH and/or —SH groups, but vinyloxycarbonyl-protected amino groups, under mild hydrolysis conditions, e.g. by warming the completely protected acid with aqueous dioxane containing sodium carbonate. That partially deprotected intermediate can then be acylated, for example by reaction with

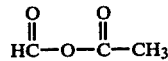

(i.e., the mixed anhydride of acetic and formic acids, prepared by reaction of 2 parts by volume of acetic anhydride with 1 part by volume of 100% formic acid at 0° C.), to give a labile formate ester or thioester. Alternatively, more stable acyl groups, e.g. lower alkanoyl such as acetyl or pivaloyl, or benzoyl can be used, in which case the acyl group will be retained in the final product of formula (I) or (II).

Once the parent acid has been suitably protected as described above to give its protected counterpart of formula (IX) or (X), then that protected acid is reacted with the alcohol of formula (IV), in the presence of a suitable dehydrating agent, as described supra, to afford the compound corresponding to formula (I) or (II), but containing protected acyloxy residues, i.e. R''—COO— as defined above in place of R—COO— in formula (I) and —OOC—R'''—COO— as defined above in place of OOC—R'—COO— in formula (II). That protected compound can then be deprotected according to the method of Olofson et al, supra, by titrating the double bond with Br₂ in methanol (neutral conditions) to give the corresponding partially deprotected compound; i.e., the resultant compound, which is obtained as the hydrobromide salt, has free amino group(s), but the —OH and/or —SH functions are still protected by acyl functions. As explained above, if the acyl functions are stable, same can be retained and no further reaction is needed to afford the final bio-affecting product of formula (I) or (II), it being recognized however that the R—COO— or —OOC—R'—COO— grouping in said product differs from the corresponding grouping in the parent acid from which it was derived in that any free reactive —OH and/or —SH groups in the parent are lower alkanoyloxy or benzoyloxy and/or lower alkanoylthio or benzoylthio in the final product. Nevertheless, such partially protected acyloxy and di(acyloxy) residues are considered to be encompassed by the definitions of R—COO— and —OOC—R'—COO— as used herein.

On the other hand, if the acyl derivatives are unstable, i.e. when a labile formate ester or thioester grouping is present, same may be deprotected by the treatment with methanol; if necessary, however, the partially deprotected hydrobromide salt may then be treated with one equivalent of ammonia in methanol to afford the totally deprotected compound of formula (I) or (II). As an illustration of this process, the following reaction sequence is given, where the starting acid is amoxicillin:

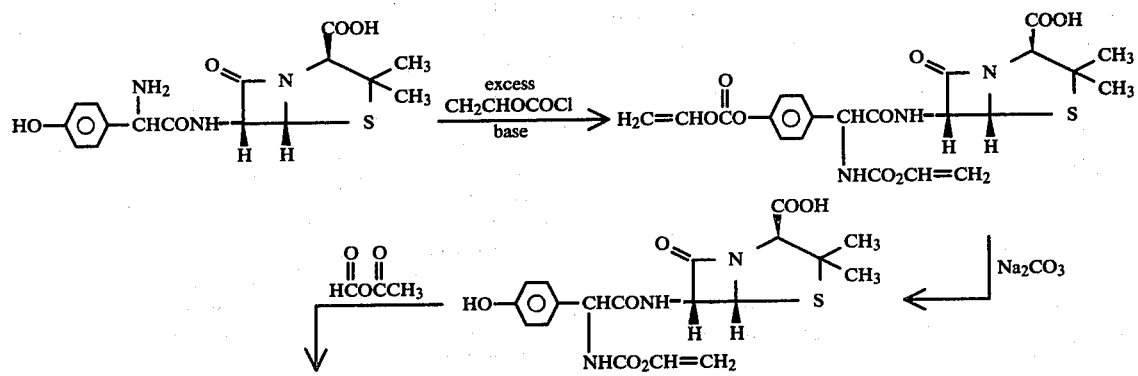

-continued

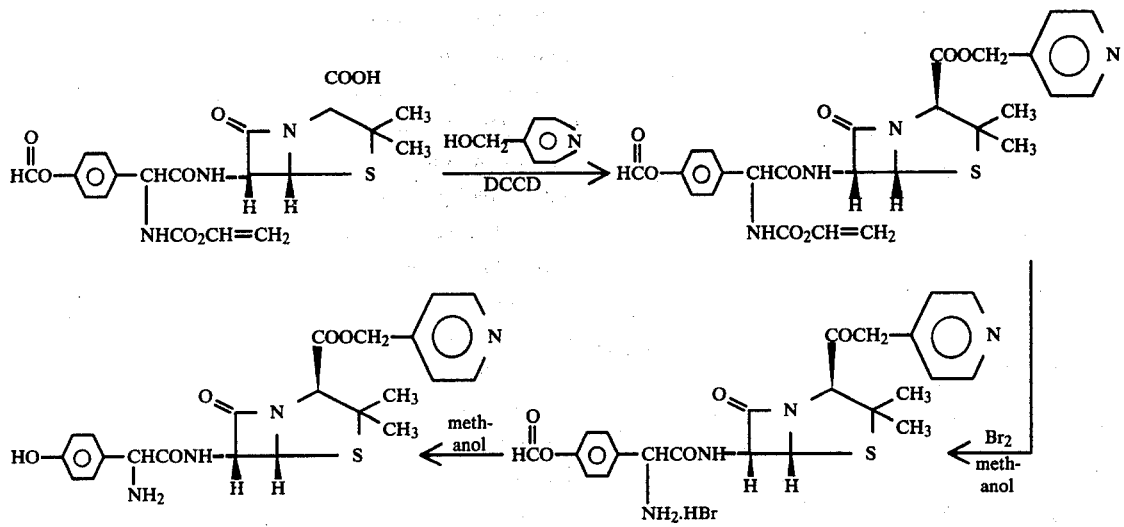

The above-described process variations involving the addition and ultimate removal of protecting groups is only used when the free amino, hydroxy and/or thiol functions are in need of protection. In some cases, for example in the case of the 11- and/or 16- and/or 17-hydroxysteroids encompassed by formula (III) hereinabove, the functional groups in question are not very reactive and would not need to be protected during the course of the reaction of the parent acid or its acid chloride with the alcohol of formula (IV).

The starting materials of formula (IV) are commercially available or can be prepared by known methods.

The compounds of the invention in which there are no functional groups requiring protection can alternatively be prepared by reacting a compound of the formula

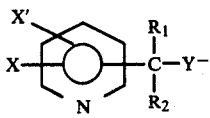
(XI)

wherein Y' is a suitable leaving group (e.g., halogen such as Cl or I or Br, or a methanesulfonyloxy or toluenesulfonyloxy group) and the remaining structural variables are defined as before, with a carboxylic acid salt of the formula

 (XII)

or

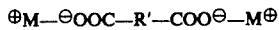 (XIII)

wherein RCOO— and —OOC—R'—COO— are defined as hereinabove and M⊕ is a suitable basic cation (e.g. sodium, potassium, thallium, etc.). Most desirably, the compound of formula (XI) is utilized in the form of its N-oxide, in which the case the resultant product is likewise in N-oxide form. Typically, the formula (XI) reactant and the selected salt are reacted in a suitable inert solvent such as benzene, dichloromethane, dimethylformamide, acetone, tetrahydrofuran, dioxane or the like, for from 1 to 8 hours, at from room temperature to reflux. The suspension is then filtered and the filtrate is evaporated to give the corresponding compound of the invention. Obviously, when a formula (XIII) reactant is used, 2 moles of pyridine compound are required per mole of metallic salt.

The formula (XII) and (XIII) starting materials used in the above procedure are prepared from the corresponding monocarboxylic and dicarboxylic acids, respectively, by treatment with base, e.g. sodium hydroxide. The formula (XI) starting materials are commercially available or can be prepared by known methods.

An alternate process for the preparation of the compounds of the invention in which there are no functional groups requiring protection utilizes a carboxylic acid starting material of formula (V) or (VII) and an acid addition salt of a compound of formula (XI) as starting materials. Typically, in the case of the formula (V) starting materials, two equivalents of an organic base such as triethylamine, tetramethylguanidine, pyridine or the like are mixed with the formula (V) acid in a polar aprotic solvent (e.g. dimethylformamide, dioxane, etc.) and that mixture is then allowed to react with the acid addition salt of a compound of formula (XI), at a temperature of from room temperature to reflux, for a period of about 1 to 8 hours. The organic base consumes the acid addition salt portion of the formula (XI) reactant, as well as the H+ and Y⁻ ions which result from the reaction itself, affording a total of two moles of organic base salt. That salt is removed by filtration, the filtrate is evaporated and the residue is purified as discussed hereinabove. In the case of the formula (VII) starting materials, i.e., the dicarboxylic acids, two moles of an acid addition salt of a compound of formula (XI) and four moles of organic base are utilized per mole of dicarboxylic acid. In either case, the final product is obtained in the form of the free base of formula (I) or (II).

As a variation of the process discussed in the preceding paragraph, the formula (XI) compound can be utilized in the form of its N-oxide acid addition salt, which can first be reacted with one mole of organic base in a suitable solvent to form the organic base salt and the formula (XI) N-oxide. The salt is removed by filtration and the filtrate is concentrated to give the N-oxide of the formula (XI) compound. That N-oxide is then subjected to the procedure described in the preceding paragraph. However, only half as much organic base is required in this case, since the organic base is only needed to consume the H+ and Y− resulting from the reaction itself, there being no acid addition salt present in the starting material. The final compound of formula (I) or (II) is thus obtained in the form of its N-oxide.

A particularly desirable alternate route to selected compounds of the invention, most especially to those compounds of formula (I) wherein R—COO— is the acyloxy residue of a cephalosporin antibiotic having one carboxylic acid function and to those compounds of formula (II) wherein —OOC—R′—COO— is the di(acyloxy) residue of a cephalosporin antibiotic having two carboxylic acid functions, involves preparation of activated thiol esters of the parent carboxylic acids as intermediates to the desired compounds of the invention, accordng to the method of Matsueda, "A Mild and Efficient Method for the Esterification of Cephalosporanic Acids", *Chemistry Letters*, 1978, pp. 979–982, published by the Chemical Society of Japan. In the first step, an organic base salt (e.g. N-methylmorpholinium or triethylammonium salt) of the parent acid of formula (V) or (VII) is reacted with 3-nitro-2-pyridinesulfenyl chloride and triphenylphosphine in a suitable inert halogenated solvent such as dichloromethane at about 0° C. for from about 0.5 to about 3 hours. (See Matsueda et al, "A Stable Pyridinesulfenyl Halide", *Chemistry Letters*, 1978, pp. 951–952, published by the Chemical Society of Japan, for a description of the preparation of the pyridinesulfenyl halide starting material.) The reaction mixture is then washed with saturated sodium bicarbonate solution, dried over sodium sulfate and concentrated to give the corresponding activated ester intermediate of the formula

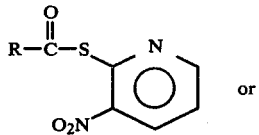

(XIV)

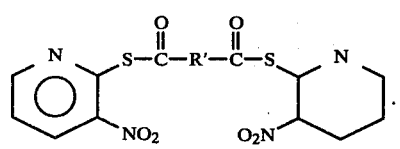

(XV)

In the second step, the activated ester of formula (XIV) or (XV) is reacted with the desired hydroxymethylpyridine of formula (IV) in an inert halogenated solvent such as dichloromethane, at a temperature of from about room temperature to −20° C., for from one to seven days. The reaction mixture is then washed with saturated sodium bicarbonate solution and water, dried over sodium sulfate and concentrated to give the corresponding compound of formula (I) or (II), which may be purified as described hereinabove. This procedure is especially advantageous when applied to the synthesis of the cephalosporin derivatives when one does not want the double bond to migrate from the 3- to the 2-position. However, the process is generally applicable to the preparation of any of the compounds of the invwention which do not require amino and/or hydroxy and/or thiol protecting groups. Indeed, the process can even be adapted to the preparation of compounds which do require such protecting groups, for example, by combining it with the vinyl chloroformate process described hereinabove. Thus, for example, the vinyloxycarbonyl protecting group (and/or other suitable protecting groups) can be introduced into the parent acid (e.g., cephalexin), giving a protected acid of formula (IX) or (X), which can then be reacted with 3-nitro-2-pyridinesulfenyl chloride to give the corresponding protected activated ester intermediate of the formula

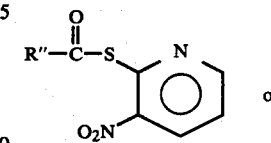

(XVI)

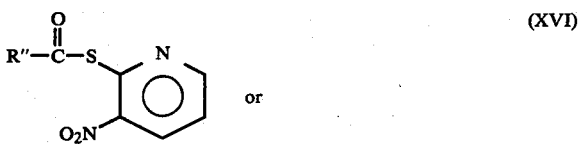

(XVII)

which is then reacted with the desired hydroxymethylpyridine of the formula (IV) as described supra to the give corresponding ester of the formula

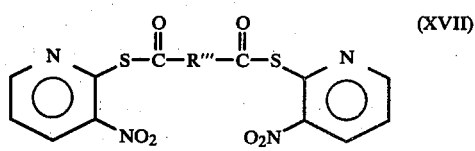

(XVIII)

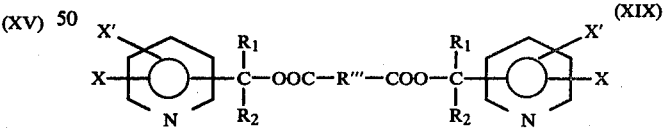

(XIX)

from which the protecting groups can be removed, as described hereinabove, to give the desired compound of formula (I) or (II).

When the starting acid of formula (V) hereinabove is a steroidal acid of formula (III), same can be prepared by methods known in the art, for example by the methods described in U.S. Pat. No. 4,164,504 (Varma). See also *Chemical Abstracts*, 83, 179407 and 84, 122146. Thus, the following reaction scheme is illustrative of a general method for preparing the desired acids:

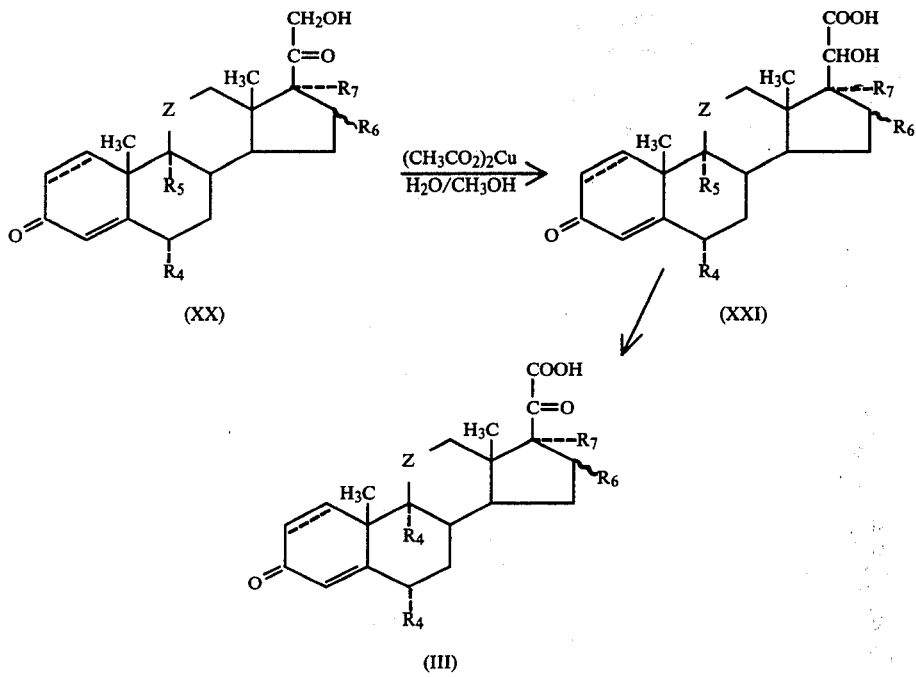

wherein R₄, R₅, R₆, R₇, Z and the dotted and wavy lines are defined as before. In the cupric acetate reaction, water is used as a co-solvent with a suitable alcohol, e.g. methanol or other lower alkanol, and the reaction is allowed to proceed for an extended period of time (more than 24 hours), since decreasing the water present and lessening reaction time tend to favor formation of the 21-ester of the steriod with the alcohol employed. Also, oxygen or air is bubbled through the mixture during the course of the reaction to encourage formation of 21-acid rather than 21-aldehyde. In the second step, the 20-hydroxy group is oxidized to a 20-keto function by reacting the steroid of formula (XXI) with manganese dioxide or lead dioxide in a inert halogenated hydrocarbon solvent such as chloroform or dichloromethane.

It will be appreciated that the compounds according to the present invention exhibit all of the biological and therapeutic activity of their "parent" drug species, for the treatment of whatever disease state or condition is known to be responsive to administration of the parent acid or its salts or esters, at the same time being characterized by enhanced biphasic solubility, bioavailability and stability under acidic conditions, while at the same time being less irritating and more permeable through biological membranes and being characterized by being easily cleaved in vivo to essentially non-toxic moieties after achieving their desired therapeutic role.

The dose of the instant compound administered, whether orally, topically, intravenous solution, or the like, and whether a single dose or a daily dose, will, of course, vary with the size and needs of the individual, the identity of the compound and the condition for which it is administered. Moreover, the dosage administered is not subject to definite bounds, but will usually be an effective amount, or the equivalent on a molar basis of the pharmacologially active form produced upon the metabolic release of the active, parent acid to achieve its desired and physiological effect, for example, depending on the nature of the parent drug, an anti-inflammatory effective amount, an analgesic effective amount, an antihypertensive effective amount, etc. of the selected compound. See *Physicians' Desk Reference*, 31 (1977). Moreover, for any of the broad spectrum of dosage forms into which the subject drugs can be formulated, i.e., any of the dosage forms into which the parent acids or their esters or salts can be formulated, see *Remington's Pharmaceutical Sciences*, 14th Edition (1970).

The pharmaceutically useful compounds of the present invention are conveniently administered to warm-blooded animals via conventional administration, most conveniently by combining the selected compound with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 14th Edition (1970). In a typical preparation for oral administration, e.g., tablet or capsule, (e.g., as an anti-inflammatory or antibiotic), one of the orally effective compounds of the instant invention (preferably in the form of its hydrochloride or other appropriate acid addition salt, or in the form of its quaternary ammonium salt formed by reacting the free base with a suitable agent such as dimethylsulfate or octyliodide) is combined in an effective amount with any suitable oral non-toxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, e.g. as an anti-inflammatory agent, any one of the compounds of the instant invention which exhibits such activity topically (preferably in the form of its free base or N-oxide) is combined with a topical vehicle such as triacetin, such that the active ingredient is present in an effective amount. The preparation is simply applied topically to the inflamed area, whereby the therapeutically active compound is dermally absorbed at the site of inflammation.

Without further elaboration, it is believed that one of ordinary skill in the art can, using the preceding description, utilize the present invention to its fullest extent. Therefore, the following examples are to be construed as merely illustrative and not limitative of the remainder of the specification and claims in any way whatsoever.

EXAMPLE 1

Preparation of (4''-Pyridyl)methyl 1-(4'-Chlorobenzoyl)-5-methoxy-2-methyl-3-indolylacetate Indomethacin (3.58 g, 0.01 mole) and 4-hydroxymethyl pyridine (1.09 g, 0.01 mole) were dissolved in 100 mL of dichloromethane and combined with 2.18 g (0.0105 mole) of dicyclohexylcarbodiimide. The suspension that resulted was stirred overnight at room temperature, then was filtered. The filtrate was concentrated and the residue was triturated with 100 mL of warm ether, then was quickly filtered. That filtrate was cooled. The crystals which formed were separated and dried to give 2.95 g (mp 130°–137° C.) of the desired compound. The product was recrystallized from tetrahydrofuran/ether (10:60 mL) to give 2.30 g (mp 136°–137.5° C., 51% yield) as analytically pure ester: $^1$H NMR (CDCl$_3$) $\delta$8.5–8.4 (m, 2, CH=C$\underline{H}$—N), 7.5 (ABq, 4, J=6 Hz, $\Delta_{\nu AB}$=14 Hz, aromatic-$\underline{H}$), 7.2–7.05 (m, 2, N—CH=C$\underline{H}$), 7.0–6.5 (m, 3, aromatic-H), 5.13 (s, 2, CO$_2$C$\underline{H}_2$), 3.8 (s, 5, C$\underline{H}_3$—O and C$\underline{H}_2$—CO$_2$) and 2.4 (s, 3, C$\underline{H}_3$—C=C).

Anal. Calcd for C$_{25}$H$_{21}$N$_2$O$_4$Cl: C, 66.89; H, 4.72; N, 6.24. Found: C, 66.98; H, 4.90; N, 5.91.

The product, which can also be named as 1-(4'-chlorobenzoyl)-5-methoxy-2-methylindole-3-acetic acid (4''-pyridyl)methyl ester, has the following structural formula:

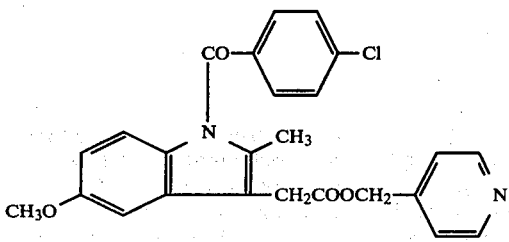

EXAMPLE 2

Preparation of (4'-Pyridyl)methyl 2-(4-Isobutylphenyl)propionate Methanesulfonate A mixture of 2.06 g (0.01 mole) of ibuprofen and 1.6 g (0.01 mole) of 4-picolyl chloride hydrochloride suspended in 15 mL of dimethylformamide was combined with 2.3 g (0.02 mole) of tetramethylguanidine. The reaction mixture was maintained at 90° C. for 2 hours, then the solvent was removed by evaporation and the residue was suspended in 200 mL of ethyl acetate. The ethyl acetate was removed by evaporation and the residue was again suspended in ethyl acetate (200 mL). The suspension was extracted with water (50 mL) and sodium bicarbonate solution (50 mL), then with water (50 mL) again. The ethyl acetate was separated, dried over sodium sulfate and concentrated to give a dark oil, which was crude 4'-pyridylmethyl 2-(4-isobutylphenyl)propionate. The oil (0.8 g, 0.027 mole) was dissolved in 10 mL of dichloromethane and 0.26 g (0.027 mole) of methanesulfonic acid was added. After ten minutes, 10 mL of tetrahydrofuran was added and the solution was cooled to give 0.84 g (mp 123°–127° C., 22% yield) of the desired product: IR (KBr) 1740 cm$^{-1}$ (C=O); $^1$H NMR (CDCl$_3$) $\delta$8.2 (ABq, 4, J=6 Hz, $\Delta_{\nu AB}$=73, aromatic-$\underline{H}$), 7.13 (s, 4, aromatic-$\underline{H}$), 5.3 (sharp m, 2, CO$_2$C$\underline{H}_2$), 4.0–3.6 (m, 1, C$\underline{H}$—CO$_2$), 2.86 (s, 3, C$\underline{H}_3$SO$_3$), 2.45 (d, J=6 $\underline{H}$z, 2, CH$_2$-aromatic), 2.0–1.5 (m, 1, CH-CH$_2$-aromatic, 1.5 (d, J=6 Hz, 3, C$\underline{H}_3$CHCO$_2$H), 0.9 (d, J=6 Hz, 6, (CH$_3$)$_2$CH).

Anal. Calcd. for C$_{20}$H$_{27}$NO$_5$S: C, 61.04; H, 6.92; N, 3.56. Found: C, 61.00; H, 6.95; N, 3.40.

The product, which can also be named as 2-(4-isobutylphenyl)propionic acid (4'-pyridyl)methyl ester methanesulfonate, is further characterized by the following structural formula:

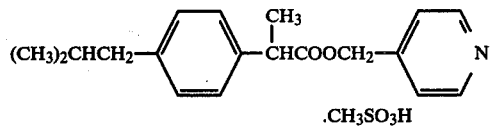

EXAMPLE 3

Preparation of (2-Benzoyloxymethyl)pyridine N-oxide

To 2.00 g (0.02 mole) of triethylamine in 6 mL of methanol were added 3.60 g (0.02 mole) of (2-chloromethyl)pyridine N-oxide hydrochloride. After several minutes, that solution was diluted with 125 mL of ether. Then, after an additional 15 minutes, the suspension was filtered. The filtrate was concentrated in vacuo to give 2.5 g (87% yield) of (2-chloromethyl)pyridine N-oxide: NMR (CDCl$_3$) $\delta$8.4–8.2 (m, 1, aromatic $\underline{H}$), 7.8–7.2 (m, 3, aromatic $\underline{H}$) and 4.8–4.7 (s, 2, C$\underline{H}_2$Cl). Next, 0.73 g (0.0060 mole) of benzoic acid was added to 0.64 g (0.0063 mole) of triethylamine dissolved in 3.0 ml of dimethylformamide. Then 0.86 g (0.0063 mole) of (2-chloromethyl)pyridine N-oxide was added and the reaction mixture was stirred at room temperature overnight. The suspension was diluted with 165 mL of ethyl acetate and the ethyl acetate solution was washed with 25 mL of water, dried over sodium sulfate and concentrated in vacuo to give 0.70 g of the crude product. The crude product was crystallized from cyclohexane to give 0.46 g (mp 125°–126° C., 33% yield) of analytically pure ester: TLC (silica gel, acetone) $R_f$ 0.36; IR (KBr) 1720 cm$^{-1}$ (s) (C=O); NMR (CDCl$_3$) $\delta$ 8.3–8.0 (m, 3, aromatic H), 7.6–7.1 (m, 7, aromatic H), and 5.6 (s, 2, CH$_2$—O$_2$C).

Anal. Calcd for C$_{13}$H$_{11}$NO$_3$: C, 68.11; H, 4.84; N, 6.11. Found: C, 68.02; H, 4.74; N, 5.92.

The product, which can also be named as benzoic acid (2-pyridyl)methyl ester N-oxide, has the structural formula:

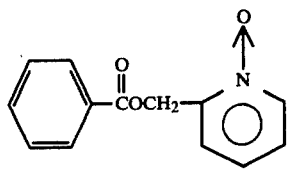

The following compounds of the invention are also prepared utilizing the processes generally or specifically described herein, for example, the methods of Examples 1, 2 or 3, or their obvious chemical equivalents. It should be noted that when the final products have free amino and/or hydroxy and/or thiol groups, those products are obtained by first forming the N- and/or O- and/or S- protected derivatives of the parent acids as generally described hereinabove, preferably via the vinyl chloroformate route, then reacting those acids having protected amino, hydroxy and/or thiol functions with the appropriate alcohol of formula (IV) in the presence of a suitable dehydrating agent (e.g. as described in Example 1), and then removing the protecting groups as generally described hereinabove to afford the desired compounds of the invention. It should be further noted that the cephalosporin derivatives are preferably prepared by transesterification of the corresponding 3-nitro-2-pyridinethiol esters of formula (XIV) or (XV) as generally discussed hereinabove; if necessary, that process is combined with the vinyl-chloroformate route as also described above. Also, as will be obvious to those skilled in the art, the amounts of reactants used in any of the processes will depend on whether the compound is derived from an acid having 1 or 2 carboxylic acid groups. Finally, where the compounds are indicated to be N-oxides, same are prepared by the method of Example 3 when there are no reactive groups in the starting materials which require protection. When such reactive groups are present, the free base is first obtained via protected intermediates as discussed supra and is then converted to its N-oxide by reaction with m-chloroperbenzoic acid or the like. The acid addition and quaternary ammonium salts are likewise obtained by first preparing the free base of formula (I) or (II) and then converting it to the desired salt as generally described hereinabove.

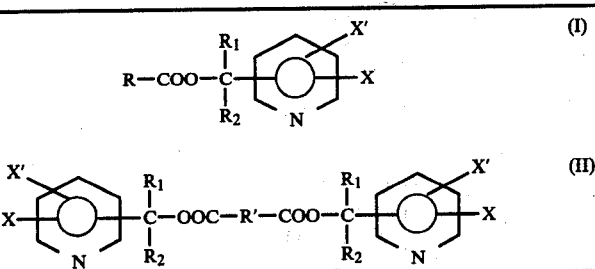

Compounds of Formula (I):

| Example Number | R—COO— is the monoacyloxy residue of | R$_1$ | R$_2$ | (pyridyl group with X', X) |
|---|---|---|---|---|
| 4 | indomethacin | H | H | N-oxide pyridyl |
| 5 | indomethacin | H | H | pyridyl |
| 6 | indomethacin | H | H | pyridyl·HCl |
| 7 | indomethacin | H | H | N-methyl pyridinium CH$_3$SO$_4^-$ |

-continued $$\text{R—COO—}\underset{R_2}{\overset{R_1}{\underset{|}{C}}}\text{—}\underset{N}{\overset{X'}{\underset{}{\bigcirc}}}\text{—X} \qquad (I)$$

$$\text{X}\text{—}\underset{N}{\overset{X'}{\underset{}{\bigcirc}}}\text{—}\underset{R_2}{\overset{R_1}{\underset{|}{C}}}\text{—OOC—R'—COO—}\underset{R_2}{\overset{R_1}{\underset{|}{C}}}\text{—}\underset{N}{\overset{X'}{\underset{}{\bigcirc}}}\text{—X} \qquad (II)$$

| # | R-COOH | R₁ | R₂ | Heterocycle |
|---|--------|----|----|-------------|
| 8 | indomethacin | H | H | 2-methyl-N-octylpyridinium iodide |
| 9 | indomethacin | H | CH₃ | 4-methylpyridine N-oxide |
| 10 | indomethacin | H | — | 4-phenylpyridine |
| 11 | indomethacin | H | H | 2,6-dimethylpyridine |
| 12 | indomethacin | CH₃ | H | 2,6-dimethylpyridine |
| 13 | aspirin | H | H | 4-methylpyridine |
| 14 | aspirin | H | H | pyridine |
| 15 | aspirin | H | H | 4-methylpyridine N-oxide |
| 16 | aspirin | H | H | pyridine·HCl |
| 17 | aspirin | H | CH₃ | 2,N-dimethylpyridinium methylsulfate |
| 18 | aspirin | H | — | 2-methyl-4-phenylpyridine |

-continued $$R-COO-\underset{R_2}{\overset{R_1}{\underset{|}{\overset{|}{C}}}}-\underset{N}{\overset{X'}{\underset{}{\bigcirc}}}-X \quad (I)$$

$$X-\underset{N}{\overset{X'}{\underset{}{\bigcirc}}}-\underset{R_2}{\overset{R_1}{\underset{|}{\overset{|}{C}}}}-OOC-R'-COO-\underset{R_2}{\overset{R_1}{\underset{|}{\overset{|}{C}}}}-\underset{N}{\overset{X'}{\underset{}{\bigcirc}}}-X \quad (II)$$

| #  | R         | R$_1$ | R$_2$ | ring |
|----|-----------|-------|-------|------|
| 19 | naproxen  | H     | H     | pyridine (4-) |
| 20 | naproxen  | H     | H     | pyridine N-oxide |
| 21 | naproxen  | H     | H     | pyridine·HCl |
| 22 | naproxen  | H     | H     | N-methyl pyridinium CH$_3$SO$_4^-$ |
| 23 | naproxen  | CH$_3$| H     | 2-methylpyridine |
| 24 | sulindac  | H     | H     | N-methyl pyridinium CH$_3$SO$_4^-$ |
| 25 | sulindac  | H     | CH$_3$| 2-methylpyridine |
| 26 | sulindac  | H     | H     | pyridine |
| 27 | sulindac  | H     | H     | pyridine N-oxide |
| 28 | sulindac  | H     | H     | 2-phenylpyridine·HCl |
| 29 | tolmetin  | H     | H     | pyridine·CH$_3$SO$_3$H |

-continued
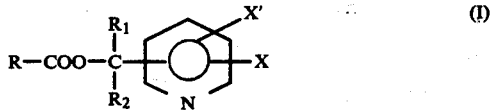 (I)
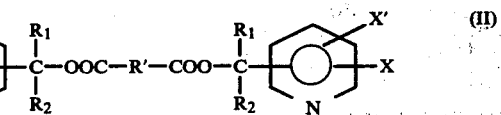 (II)
| | | R₁ | R₂ | |
|---|---|---|---|---|
| 30 | tolmetin | H | H | 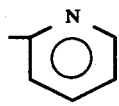 |
| 31 | tolmetin | H | H | 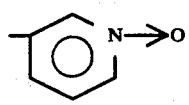 |
| 32 | tolmetin | H | CH₃ |  |
| 33 | tolmetin | H | H | 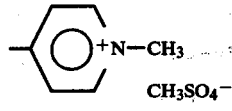 |
| 34 | diflunisal | H | H |  |
| 35 | diflunisal | H | H | 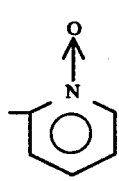 |
| 36 | diflunisal | H | CH₃ | 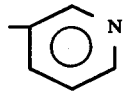 |
| 37 | diflunisal | H | H | 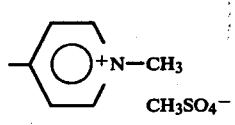 |
| 38 | diflunisal | ⌬ | H | 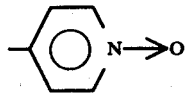 |
| 39 | flurbiprofen | H | H | 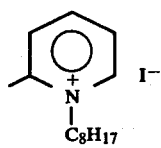 |

-continued $$\text{R—COO—}\underset{R_2}{\overset{R_1}{\text{C}}}\text{—}\underset{\underset{N}{\phantom{X}}}{\overset{X'}{\bigcirc}}\text{X} \quad (I)$$

$$\underset{\underset{N}{\phantom{X}}}{\overset{X'}{\bigcirc}}\text{X—}\underset{R_2}{\overset{R_1}{\text{C}}}\text{—OOC—R'—COO—}\underset{R_2}{\overset{R_1}{\text{C}}}\text{—}\underset{\underset{N}{\phantom{X}}}{\overset{X'}{\bigcirc}}\text{X} \quad (II)$$

| No. | Compound | R₁ | R₂ | Pyridine |
|---|---|---|---|---|
| 40 | flurbiprofen | H | H | pyridin-4-yl |
| 41 | flurbiprofen | H | H | 6-methylpyridin-2-yl (2-CH₃) |
| 42 | flurbiprofen | H | CH₃ | 6-methylpyridin-2-yl |
| 43 | flurbiprofen | H | H | pyridinyl · HCl |
| 44 | indoprofen | H | H | pyridin-4-yl N→O |
| 45 | indoprofen | H | H | 1-methylpyridinium-4-yl, CH₃SO₄⁻ |
| 46 | indoprofen | H | H | 2-methylpyridin-? · HCl |
| 47 | indoprofen | H | H | pyridin-4-yl |
| 48 | indoprofen | CH₃ | H | 6-methylpyridin-2-yl |
| 49 | fenclozic acid | H | H | pyridin-2-yl |
| 50 | fenclozic acid | H | H | pyridin-4-yl N→O |

-continued $$R-COO-\underset{R_2}{\overset{R_1}{\underset{|}{C}}}-\underset{\underset{N}{\bigcirc}}{\overset{X'}{\bigcirc}}-X \quad (I)$$

$$X-\underset{\underset{N}{\bigcirc}}{\overset{X'}{\bigcirc}}-\underset{R_2}{\overset{R_1}{\underset{|}{C}}}-OOC-R'-COO-\underset{R_2}{\overset{R_1}{\underset{|}{C}}}-\underset{\underset{N}{\bigcirc}}{\overset{X'}{\bigcirc}}-X \quad (II)$$

| # | Compound | R₁ | R₂ | Pyridine group |
|---|---|---|---|---|
| 51 | fenclozic acid | H | H | pyridine·HCl |
| 52 | fenclozic acid | CH₃ | H | N-methylpyridinium CH₃SO₄⁻ |
| 53 | fenclozic acid | H | phenyl | 2-methylpyridine |
| 54 | ketoprofen | H | H | pyridine N-oxide |
| 55 | ketoprofen | H | H | pyridine·HCl |
| 56 | ketoprofen | H | H | N-octylpyridinium I⁻ |
| 57 | ketoprofen | CH₃ | H | pyridine |
| 58 | ketoprofen | H | phenyl | 2-methylpyridine N-oxide |
| 59 | alclofenac | H | H | pyridine N-oxide |
| 60 | alclofenac | H | H | N-methylpyridinium CH₃SO₄⁻ |

-continued $$R-COO-\underset{R_2}{\underset{|}{\overset{R_1}{\underset{|}{C}}}}-\underset{N}{\overset{X'}{\bigcirc}}-X \quad (I)$$

$$\underset{N}{\overset{X'}{\bigcirc}}-X \quad \underset{R_2}{\underset{|}{\overset{R_1}{\underset{|}{C}}}}-OOC-R'-COO-\underset{R_2}{\underset{|}{\overset{R_1}{\underset{|}{C}}}}-\underset{N}{\overset{X'}{\bigcirc}}-X \quad (II)$$

| # | acid | R₁ | R₂ | ring |
|---|------|-----|-----|------|
| 61 | alclofenac | H | CH₃ | pyridine (N top) |
| 62 | alclofenac | H | H | 2-methylpyridine |
| 63 | alclofenac | phenyl | H | pyridine·HCl |
| 64 | bucloxic acid | H | H | pyridine |
| 65 | bucloxic acid | H | H | pyridine N-oxide |
| 66 | bucloxic acid | H | CH₃ | piperidine·HCl |
| 67 | bucloxic acid | phenyl | H | N-methylpyridinium CH₃SO₄⁻ |
| 68 | bucloxic acid | H | H | pyridine |
| 69 | cinchophen | H | H | pyridine·CH₃SO₃H |
| 70 | cinchophen | H | H | pyridine N→O |
| 71 | cinchophen | CH₃ | H | N-methylpyridinium CH₃SO₄⁻ |

-continued
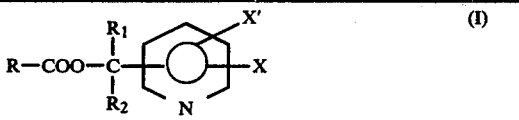  (I)
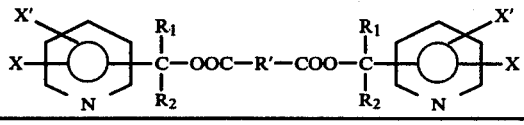  (II)
| | | R₁ | R₂ | |
|---|---|---|---|---|
| 72 | cinchophen | H | H | 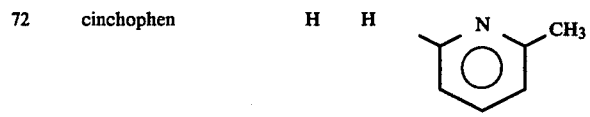 |
| 73 | cinchophen | H | |  |
| 74 | pirprofen | H | H | 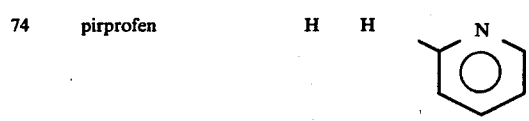 |
| 75 | pirprofen | H | H | 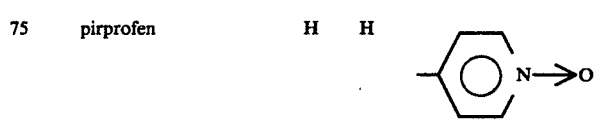 |
| 76 | pirprofen | CH₃ | H | 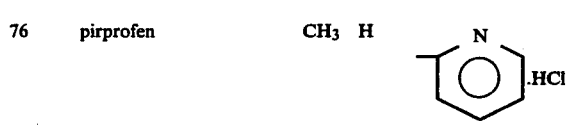 |
| 77 | pirprofen | H | H | 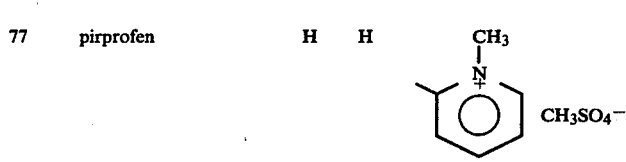 |
| 78 | pirprofen | H | |  |
| 79 | oxoprozin | H | H | 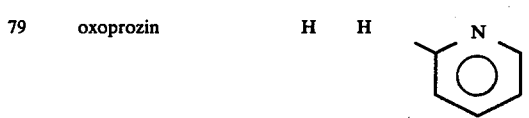 |
| 80 | oxoprozin | H | H | 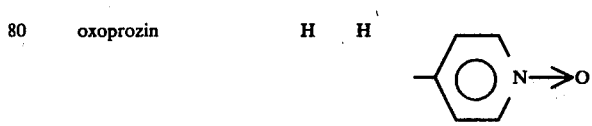 |
| 81 | oxoprozin | H | H | 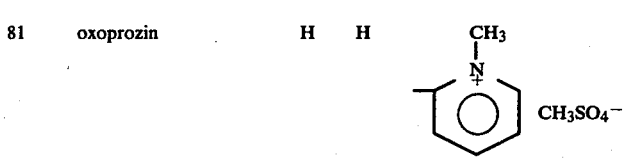 |
| 82 | oxoprozin | H | CH₃ | 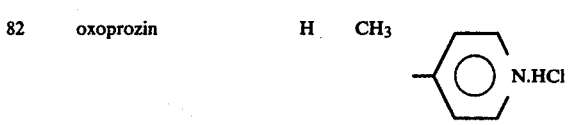 |

|   |   |   | -continued |
|---|---|---|---|
|   |   |   | 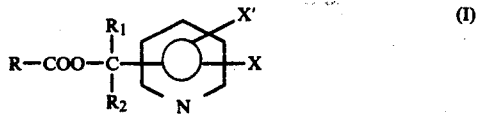 (I) |
|   |   |   | 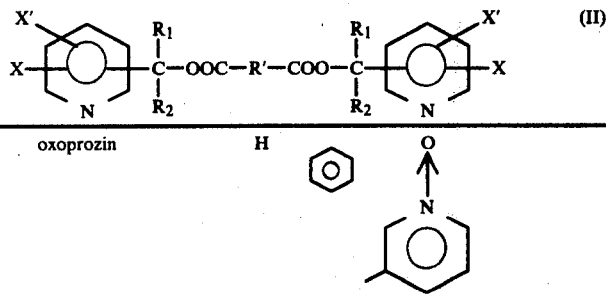 (II) |
| 83 | oxoprozin | H | 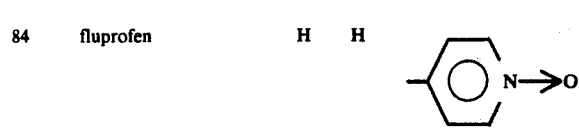 |
| 84 | fluprofen | H | H 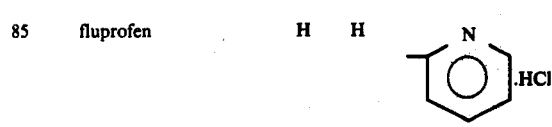 |
| 85 | fluprofen | H | H 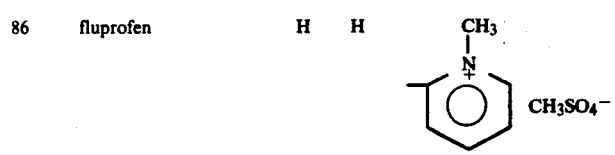 |
| 86 | fluprofen | H | H 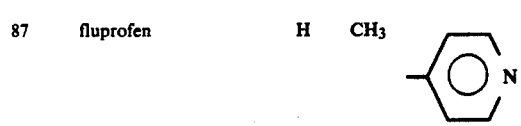 |
| 87 | fluprofen | H | CH₃ 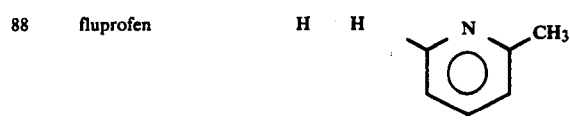 |
| 88 | fluprofen | H | H 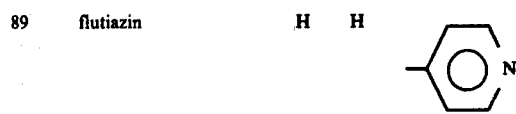 |
| 89 | flutiazin | H | H 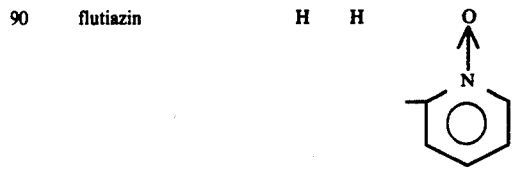 |
| 90 | flutiazin | H | H 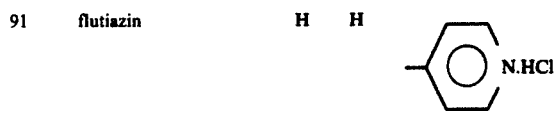 |
| 91 | flutiazin | H | H 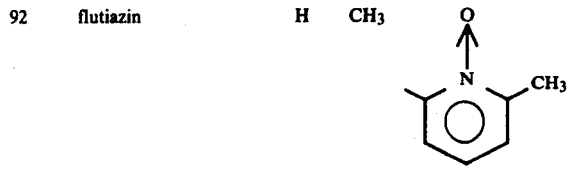 |
| 92 | flutiazin | H | CH₃ |

-continued $$R-COO-\underset{R_2}{\overset{R_1}{\underset{|}{C}}}-\underset{N}{\overset{X'}{\underset{X}{\bigcirc}}} \quad \text{(I)}$$

$$\underset{N}{\overset{X'}{\underset{X}{\bigcirc}}}-\underset{R_2}{\overset{R_1}{\underset{|}{C}}}-OOC-R'-COO-\underset{R_2}{\overset{R_1}{\underset{|}{C}}}-\underset{N}{\overset{X'}{\underset{X}{\bigcirc}}} \quad \text{(II)}$$

| | | | |
|---|---|---|---|
| 93 | flutiazin | ⬡  H | pyridyl |
| 94 | clometacin | H  H | pyridine·CH₃SO₃H |
| 95 | clometacin | CH₃  H | pyridyl |
| 96 | clometacin | H  H | pyridine N-oxide |
| 97 | clometacin | H  H | N-octylpyridinium I⁻ |
| 98 | clometacin | ⬡  H | 2-methylpyridyl |
| 99 | flufenisal | H  H | pyridine N-oxide |
| 100 | flufenisal | ⬡  H | N-C₈H₁₇ pyridinium I⁻ |
| 101 | flufenisal | H  H | pyridine·CH₃SO₃H |
| 102 | flufenisal | H  H | pyridine N→O |

-continued $$\text{R—COO—}\underset{R_2}{\overset{R_1}{\underset{|}{\overset{|}{C}}}}\text{—}\underset{N}{\bigcirc}\overset{X'}{\underset{X}{}} \qquad \text{(I)}$$

$$\overset{X'}{\underset{N}{\bigcirc}}\underset{X}{}\text{—}\underset{R_2}{\overset{R_1}{\underset{|}{\overset{|}{C}}}}\text{—OOC—R'—COO—}\underset{R_2}{\overset{R_1}{\underset{|}{\overset{|}{C}}}}\text{—}\underset{N}{\bigcirc}\overset{X'}{\underset{X}{}} \qquad \text{(II)}$$

| | | | | |
|---|---|---|---|---|
| 103 | flufenisal | H | CH₃ | pyridine |
| 104 | salsalate | H | H | pyridine N-oxide |
| 105 | salsalate | H | H | N-methylpyridinium CH₃SO₄⁻ |
| 106 | salsalate | CH₃ | H | 2,6-dimethylpyridine |
| 107 | salsalate | H | phenyl | pyridine |
| 108 | salsalate | H | H | pyridine·HCl |
| 109 | cinmetacin | H | H | pyridine·HCl |
| 110 | cinmetacin | H | H | N-methylpyridinium CH₃SO₄⁻ |
| 111 | cinmetacin | H | CH₃ | pyridine N-oxide |
| 112 | cinmetacin | phenyl | H | pyridine |
| 113 | cinmetacin | H | H | 2-methylpyridine |

-continued
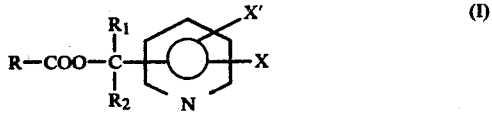 (I)
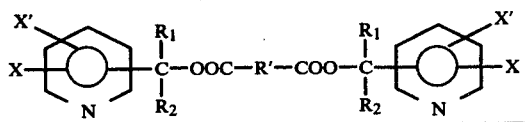 (II)
| | | | | |
|---|---|---|---|---|
| 114 | furobufen | H | H | 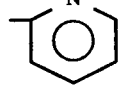 |
| 115 | furobufen | H | H | 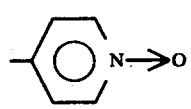 |
| 116 | furobufen | H | H | 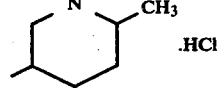 .HCl |
| 117 | furobufen | H | CH₃ | 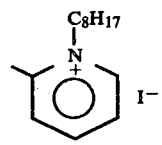 |
| 118 | furobufen | 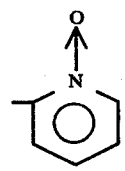 | H | 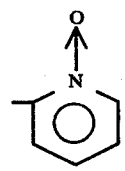 |
| 119 | prodolic acid | H | H | 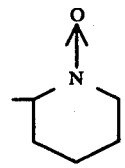 |
| 120 | prodolic acid | H | H | 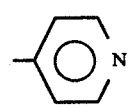 |
| 121 | prodolic acid | 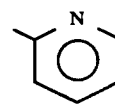 | H | 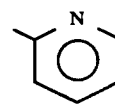 |
| 122 | prodolic acid | CH₃ | H | 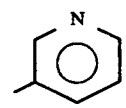 |
| 123 | prodolic acid | H | H | 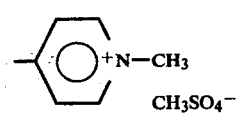 |

-continued
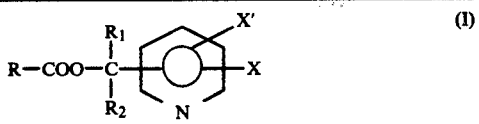 (I)
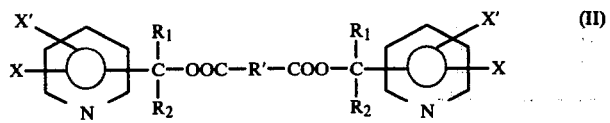 (II)
| | | R₁ | R₂ | |
|---|---|---|---|---|
| 124 | ibuprofen | H | H | 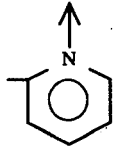 |
| 125 | ibuprofen | H | H | 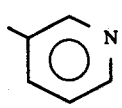 |
| 126 | ibuprofen | H | H | 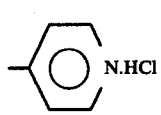 |
| 127 | ibuprofen | H | H | 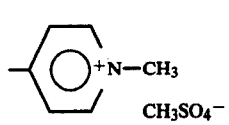 |
| 128 | ibufenac | H | H | 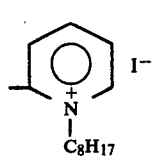 |
| 129 | ibufenac | H | CH₃ | 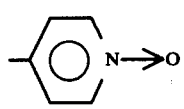 |
| 130 | ibufenac | H | | 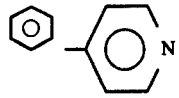 |
| 131 | ibufenac | CH₃ | H | 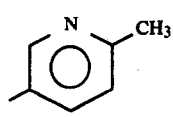 |
| 132 | ibufenac | H | H | 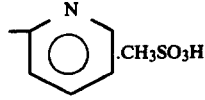 |
| 133 | cefmetazole | H | H | 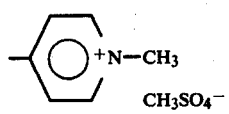 |

-continued $$R-COO-\underset{R_2}{\overset{R_1}{\underset{|}{C}}}-\underset{N}{\overset{X'}{\bigcirc}}X \quad (I)$$

$$X-\underset{N}{\overset{X'}{\bigcirc}}-\underset{R_2}{\overset{R_1}{\underset{|}{C}}}-OOC-R'-COO-\underset{R_2}{\overset{R_1}{\underset{|}{C}}}-\underset{N}{\overset{X'}{\bigcirc}}X \quad (II)$$

| | | $R_1$ | $R_2$ | |
|---|---|---|---|---|
| 134 | cefmetazole | H | H | pyridine·HCl (4-subst) |
| 135 | cefmetazole | H | H | 2-methyl-N-C$_8$H$_{17}$ pyridinium I$^-$ |
| 136 | cefmetazole | CH$_3$ | H | 2-methylpyridine |
| 137 | cefmetazole | H | phenyl | 2-methylpyridine·HCl |
| 138 | cefazolin | H | H | N-CH$_3$ pyridinium CH$_3$SO$_4^-$ |
| 139 | cefazolin | H | H | pyridine·HCl |
| 140 | cefazolin | H | H | $^+$N—C$_8$H$_{17}$ pyridinium I$^-$ |
| 141 | cefazolin | H | CH$_3$ | pyridine |
| 142 | cefazolin | phenyl | H | 2-methylpyridine·CH$_3$SO$_3$H |
| 143 | cephalexin | H | H | $^+$N—CH$_3$ pyridinium CH$_3$SO$_4^-$ |
| 144 | cephalexin | H | H | pyridine·HCl |

-continued $$\text{R—COO—}\underset{R_2}{\overset{R_1}{C}}\text{—}\underset{N}{\bigcirc}\overset{X'}{\underset{X}{}} \quad (I)$$

$$\overset{X'}{\underset{X}{\bigcirc}}\underset{N}{\text{—}}\underset{R_2}{\overset{R_1}{C}}\text{—OOC—R'—COO—}\underset{R_2}{\overset{R_1}{C}}\text{—}\underset{N}{\bigcirc}\overset{X'}{\underset{X}{}} \quad (II)$$

| No. | Compound | $R_1$ | $R_2$ | Pyridine group |
|---|---|---|---|---|
| 145 | cephalexin | H | H | 4-(N-C$_8$H$_{17}$)pyridinium I$^-$ |
| 146 | cephalexin | CH$_3$ | H | N-CH$_3$ pyridinium CH$_3$SO$_4^-$ |
| 147 | cephalexin | H | | 2-phenyl-6-methylpyridine·HCl |
| 148 | cefoxitin | H | H | pyridine·HCl |
| 149 | cephacetrile | H | H | pyridine·HCl |
| 150 | cephaloglycin | H | H | N-CH$_3$ pyridinium CH$_3$SO$_4^-$ |
| 151 | cephaloridine | H | H | 4-(N-CH$_3$)pyridinium CH$_3$SO$_4^-$ |
| 152 | cephalothin | H | H | 2-methyl-N-C$_8$H$_{17}$ pyridinium I$^-$ |
| 153 | cephapirin | H | H | 4-(N—C$_8$H$_{17}$)pyridinium I$^-$ |
| 154 | cephradine | H | H | pyridine·HCl |

-continued
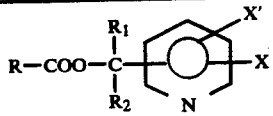 (I)
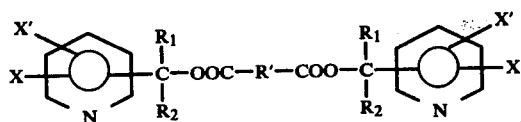 (II)
| | | R₁ | R₂ | |
|---|---|---|---|---|
| 155 | ampicillin | H | H | 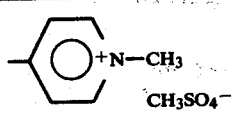 |
| 156 | ampicillin | H | H |  |
| 157 | ampicillin | H | H | 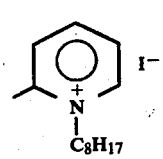 |
| 158 | ampicillin | CH₃ | H | 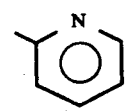 |
| 159 | ampicillin | H | 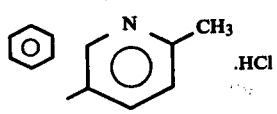 |  |
| 160 | amoxicillin | H | H | 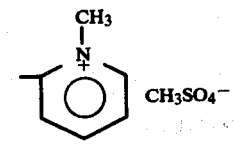 |
| 161 | amoxicillin | H | H | 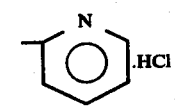 |
| 162 | amoxicillin | H | H | 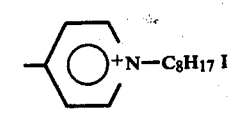 |
| 163 | amoxicillin | H | CH₃ | 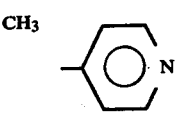 |
| 164 | amoxicillin |  | H |  |
| 165 | carfecillin | H | H | 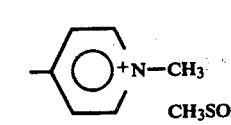 |

-continued $$R-COO-\underset{R_2}{\overset{R_1}{C}}-\text{Pyridine}(X, X') \quad (I)$$

$$(X, X')\text{Pyridine}-\underset{R_2}{\overset{R_1}{C}}-OOC-R'-COO-\underset{R_2}{\overset{R_1}{C}}-\text{Pyridine}(X, X') \quad (II)$$

| No. | Compound | R₁ | R₂ | Pyridine substituent |
|---|---|---|---|---|
| 166 | carindacillin | H | H | pyridine·HCl |
| 167 | hetacillin | H | H | N-methylpyridinium CH₃SO₄⁻ |
| 168 | hetacillin | H | H | pyridine·HCl |
| 169 | hetacillin | H | H | 2-methyl-N-octylpyridinium I⁻ |
| 170 | hetacillin | CH₃ | H | 2-methylpyridine |
| 171 | hetacillin | H | phenyl | 2-methylpyridine·HCl |
| 172 | amylpenicillin | H | H | pyridine·HCl |
| 173 | azidocillin | H | H | pyridine·HCl |
| 174 | benzylpenicillinic acid | H | H | N-methylpyridinium CH₃SO₄⁻ |
| 175 | clometacillin | H | H | N-methylpyridinium CH₃SO₄⁻ |

-continued $$\text{R—COO—}\underset{R_2}{\overset{R_1}{C}}\text{—}\underset{N}{\overset{X'}{\bigcirc}}\text{—X} \quad \text{(I)}$$

$$\text{X—}\underset{N}{\overset{X'}{\bigcirc}}\text{—}\underset{R_2}{\overset{R_1}{C}}\text{—OOC—R'—COO—}\underset{R_2}{\overset{R_1}{C}}\text{—}\underset{N}{\overset{X'}{\bigcirc}}\text{—X} \quad \text{(II)}$$

| | | $R_1$ | $R_2$ | |
|---|---|---|---|---|
| 176 | cloxacillin | H | H | 2-methyl-1-octylpyridinium iodide |
| 177 | cyclacillin | H | H | pyridine·HCl (4-) |
| 178 | methicillin | H | H | pyridine·HCl |
| 179 | nafcillin | H | H | 2-methylpyridine·HCl |
| 180 | 2-pentenyl-penicillin | H | H | pyridine·HCl (4-) |
| 181 | penicillin BT | H | H | 1-methylpyridinium methylsulfate |
| 182 | penicillin O | H | H | 1-octylpyridinium iodide (4-) |
| 183 | penicillin S | H | H | 2-methyl-1-octylpyridinium iodide |
| 184 | penicillin V | H | H | 1-methylpyridinium methylsulfate |
| 185 | penicillin V | H | H | pyridine·HCl (4-) |

-continued
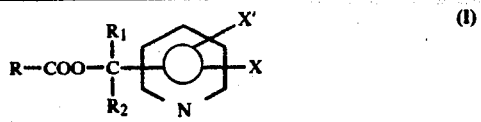 (I)
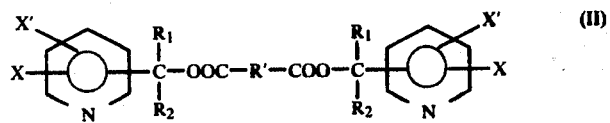 (II)
| | | R₁ | R₂ | |
|---|---|---|---|---|
| 186 | penicillin V | H | H | 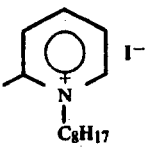 |
| 187 | penicillin V | CH₃ | H | 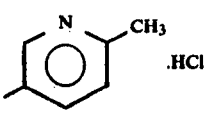 |
| 188 | penicillin V | H | |  |
| 189 | chlorobutin penicillin | H | H | 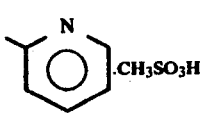 |
| 190 | dicloxacillin | H | H |  |
| 191 | diphenicillin | H | H | 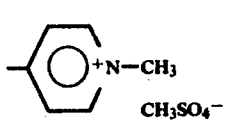 |
| 192 | heptylpenicillin | H | H | 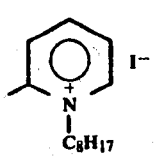 |
| 193 | metampicillin | H | H |  |
| 194 | GABA | H | H | 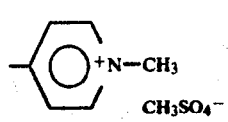 |
| 195 | GABA | H | H |  |

-continued
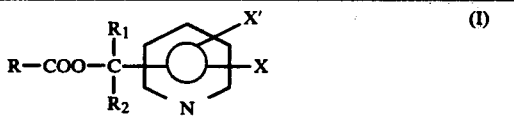 (I)
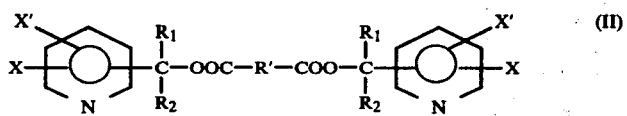 (II)
| | | | | |
|---|---|---|---|---|
| 196 | GABA | H | H | 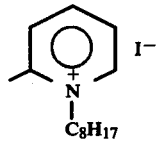 |
| 197 | GABA | H | CH$_3$ | 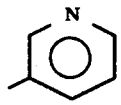 |
| 198 | GABA |  | H | 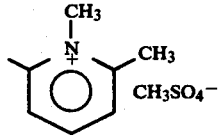 |
| 199 | captopril | H | H | 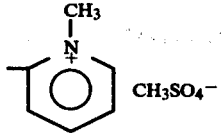 |
| 200 | captopril | H | H | 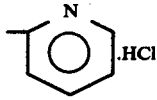 |
| 201 | captopril | H | H | 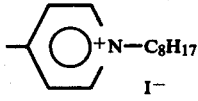 |
| 202 | captopril |  | H | 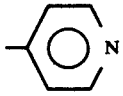 |
| 203 | captopril | H | CH$_3$ | 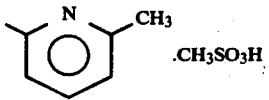 |
| 204 | valproic acid | H | H | 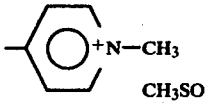 |
| 205 | valproic acid | H | H | 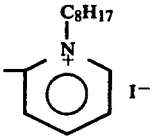 |

4,376,767
-continued
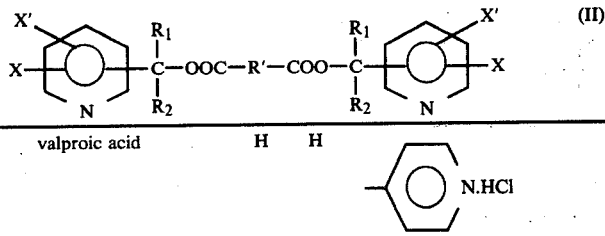
| | | $R_1$ | $R_2$ | |
|---|---|---|---|---|
| 206 | valproic acid | H | H |  |
| 207 | valproic acid | CH₃ | H | 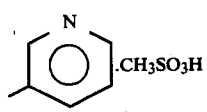 |
| 208 | valproic acid | H | H | 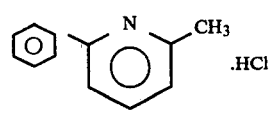 |
Compounds of Formula (II):
| Example Number | —OOC—R'—COO'— is the di(acyloxy) residue of | $R_1$ | $R_2$ | |
|---|---|---|---|---|
| 209 | methotrexate | H | H |  |
| 210 | methotrexate | H | H | 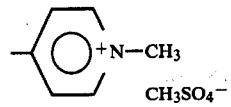 |
| 211 | methotrexate | H | H | 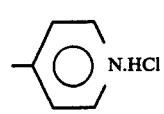 |
| 212 | methotrexate | CH₃ | H | 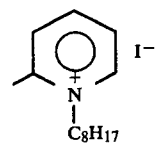 |
| 213 | methotrexate | H | H | 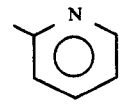 |
| 214 | carbenicillin | H | H | 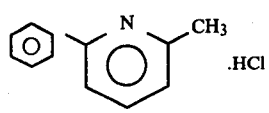 |
| 215 | carbenicillin | H | H | 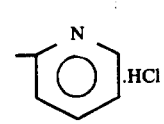 |

-continued
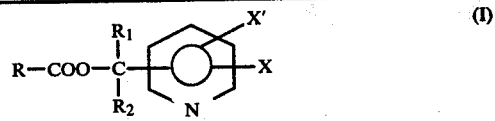 (I)
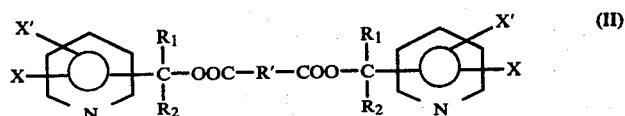 (II)
| | | R₁ | R₂ | |
|---|---|---|---|---|
| 216 | carbenicillin | H | H | 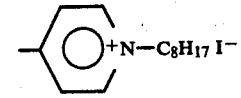 |
| 217 | carbenicillin | H | CH₃ | 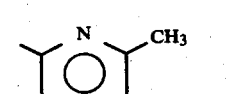 |
| 218 | carbenicillin |  | H | 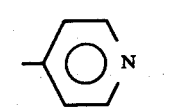 |
| 219 | penicillin N | H | H | 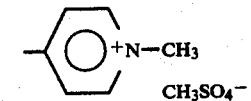 |
| 220 | penicillin N | H | H |  |
| 221 | penicillin N | H | H | 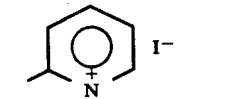 |
| 222 | penicillin N | CH₃ | H |  |
| 223 | penicillin N | H |  | 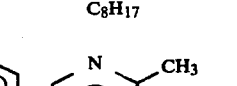 |
| 224 | cephalosporin C | H | H | 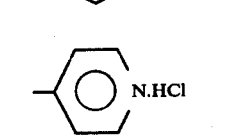 |
| 225 | cephalosporin C | H | H |  |

-continued
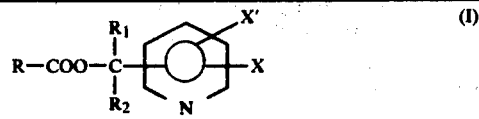 (I)
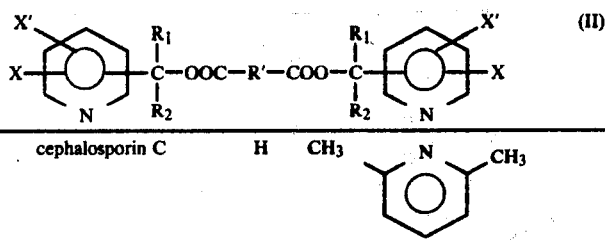 (II)
| | | $R_1$ | $R_2$ | |
|---|---|---|---|---|
| 226 | cephalosporin C | H | CH$_3$ | 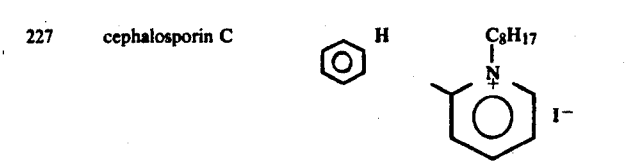 |
| 227 | cephalosporin C |  | H | |
| 228 | cephamycin A | H | H | 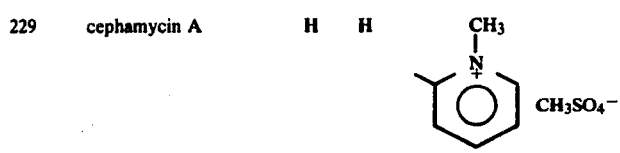 |
| 229 | cephamycin A | H | H | 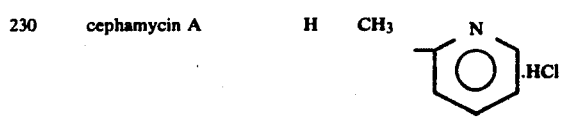 |
| 230 | cephamycin A | H | CH$_3$ |  |
| 231 | cephamycin B | H | H | 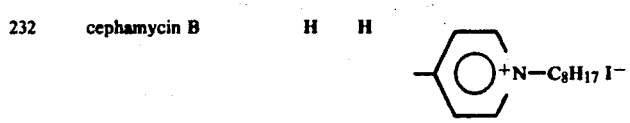 |
| 232 | cephamycin B | H | H | 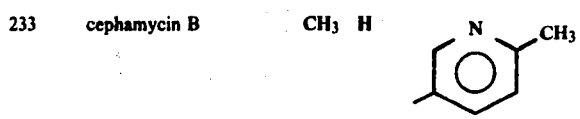 |
| 233 | cephamycin B | CH$_3$ | H | 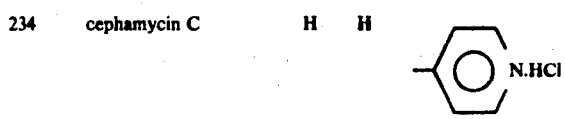 |
| 234 | cephamycin C | H | H | 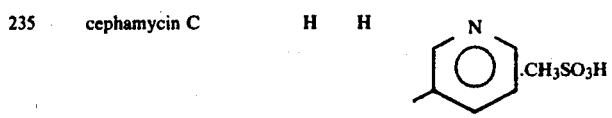 |
| 235 | cephamycin C | H | H | |
| 236 | cephamycin C | 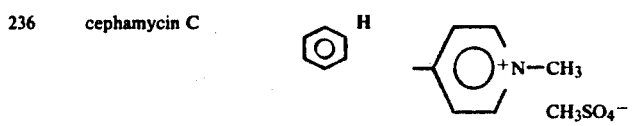 | H | |

The following compounds of the invention are also prepared utilizing the processes generally or specifically described herein, for example, the methods of Examples 1, 2 or 3, or their obvious chemical equivalents. For this group of compounds, the free hydroxy groups in the starting material [e.g. in the acid of formula (III)] are generally inert to the reaction conditions used and thus need not be protected during the acylation

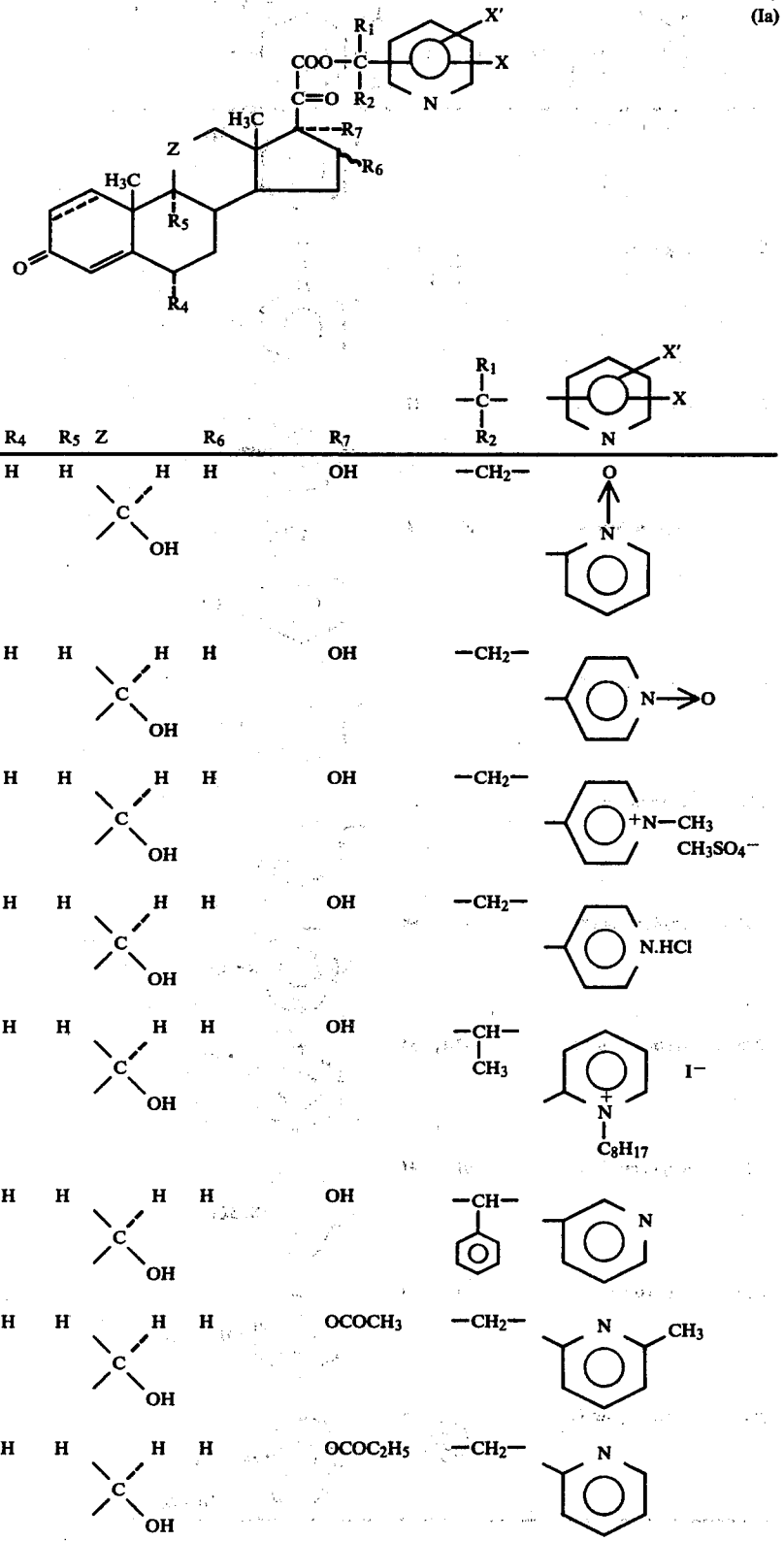

-continued

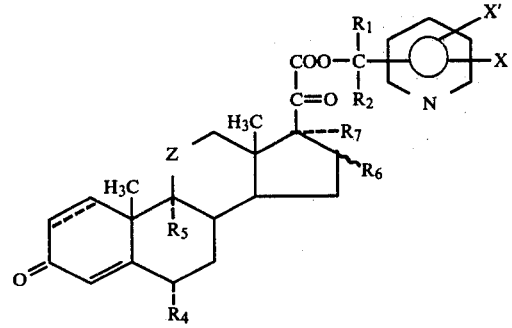

(Ia)

| Example Number | Δ¹ | $R_4$ | $R_5$ | Z | $R_6$ | $R_7$ | 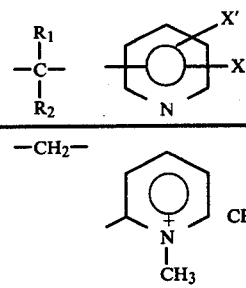 | |
|---|---|---|---|---|---|---|---|---|
| 245 | saturated | H | H | >C(H)(OH) | H | $OCOC_3H_7$ | $-CH_2-$ | 2-methyl-N-methylpyridinium $CH_3SO_4^-$ |
| 246 | saturated | H | H | >C(H)(OH) | H | $-OC(O)C_6H_5$ | $-CH_2-$ | 4-(N-$C_8H_{17}$)pyridinium $I^-$ |
| 247 | unsaturated | H | F | >C(H)(OH) | β-$CH_3$ | OH | $-CH(CH_3)-$ | 4-pyridyl |
| 248 | unsaturated | H | F | >C(H)(OH) | β-$CH_3$ | OH | $-CH_2-$ | pyridine N-oxide |
| 249 | unsaturated | H | F | >C(H)(OH) | β-$CH_3$ | OH | $-CH_2-$ | pyridyl·HCl |
| 250 | unsaturated | H | F | >C(H)(OH) | β-$CH_3$ | $OCOC_4H_9$ | $-CH_2-$ | 4-(N-$CH_3$)pyridinium $CH_3SO_4^-$ |
| 251 | unsaturated | H | F | >C(H)(OH) | β-$CH_3$ | $-OC(O)C_6H_5$ | $-CH(C_6H_5)-$ | 2-methyl-N-$C_8H_{17}$-pyridinium $I^-$ |
| 252 | unsaturated | H | F | >C(H)(OH) | α-$CH_3$ | OH | $-CH(CH_3)-$ | 2,6-dimethylpyridyl |

-continued
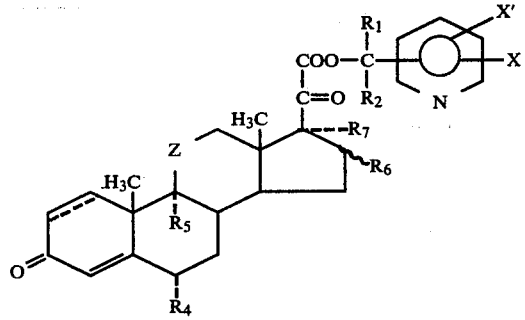
| Example Number | Δ¹ | R₄ | R₅ | Z | R₆ | R₇ | $-\underset{R_2}{\overset{R_1}{C}}-$ | pyridine substituent |
|---|---|---|---|---|---|---|---|---|
| 253 | unsaturated | H | F | 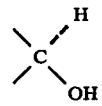 | α-CH₃ | OH | —CH₂— | 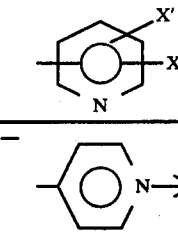 |
| 254 | unsaturated | H | F | 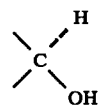 | α-CH₃ | OH | —CH₂— | 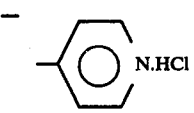 |
| 255 | unsaturated | H | F | 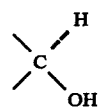 | α-CH₃ | 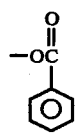 | —CH— 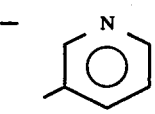 | |
| 256 | unsaturated | H | F | 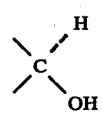 | α-CH₃ | OCOCH₃ | —CH₂— | 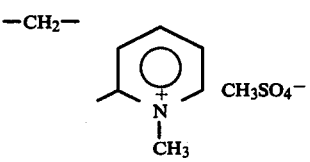 |
| 257 | unsaturated | H | H | 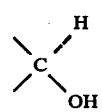 | H | OH | —CH₂— | 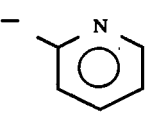 |
| 258 | unsaturated | H | H | 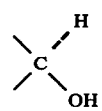 | H | OH | —CH₂— | 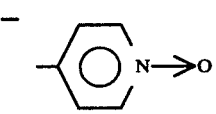 |
| 259 | unsaturated | H | H | 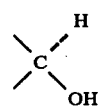 | H | OH | —CH₂— | 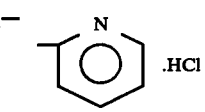 |
| 260 | unsaturated | H | H | 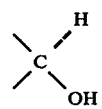 | H | 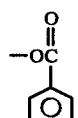 | —CH— 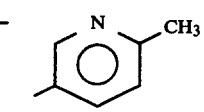 | |
| 261 | unsaturated | H | H | 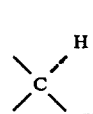 | H | OCOC₃H₇ | —CH— 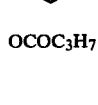 CH₃ | 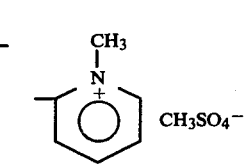 |

-continued

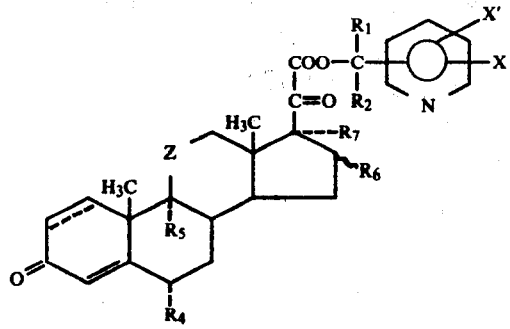
(Ia)

| Example Number | Δ¹ | $R_4$ | $R_5$ | Z | $R_6$ | $R_7$ | $-\underset{R_2}{\overset{R_1}{\underset{|}{\overset{|}{C}}}}-$ | pyridine group |
|---|---|---|---|---|---|---|---|---|
| 262 | unsaturated | H | F | >C<(H)(OH) | α-OH | OH | —CH₂— | pyridine N→O |
| 263 | unsaturated | H | F | >C<(H)(OH) | α-OH | OH | —CH₂— | pyridine |
| 264 | unsaturated | H | F | >C<(H)(OH) | α-OH | OH | —CH₂— | pyridine·HCl |
| 265 | unsaturated | H | F | >C<(H)(OH) | —O—C(CH₃)₂—O— | —CH₂— | N⁺—CH₃ CH₃SO₄⁻ |
| 266 | unsaturated | H | F | >C<(H)(OH) | —O—C(CH₃)₂—O— | —CH₂— | 2-methyl-N-C₈H₁₇ pyridinium I⁻ |
| 267 | unsaturated | H | F | >C<(H)(OH) | α-OCOCH₃ | OCOCH₃ | —CH(CH₃)— | pyridine N→O |
| 268 | unsaturated | H | F | >C<(H)(OH) | —O—C(CH₃)₂—O— | —CH(C₆H₅)— | 6-methylpyridine |
| 269 | unsaturated | F | H | >C<(H)(OH) | α-CH₃ | H | —CH₂— | pyridine |
| 270 | unsaturated | F | H | >C<(H)(OH) | α-CH₃ | H | —CH(CH₃)— | pyridine |

-continued

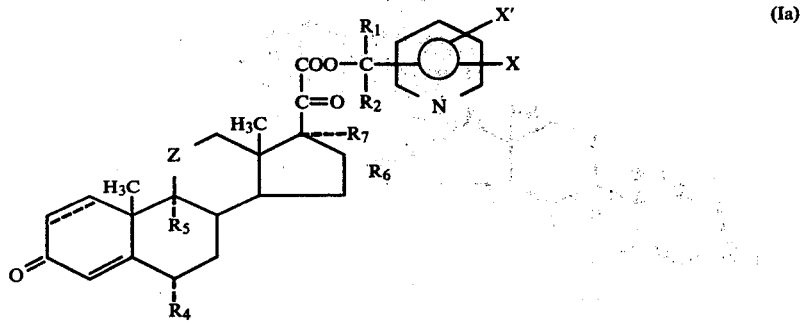
(Ia)

| Example Number | Δ¹ | $R_4$ | $R_5$ | Z | $R_6$ | $R_7$ | $-\underset{R_2}{\overset{R_1}{\underset{|}{\overset{|}{C}}}}-$ | pyridine group (with X, X') |
|---|---|---|---|---|---|---|---|---|
| 271 | unsaturated | F | H | >C(H)(OH) | α-CH₃ | H | —CH₂— | pyridine · HCl |
| 272 | unsaturated | F | H | >C(H)(OH) | α-CH₃ | H | —CH₂— | N-methylpyridinium CH₃SO₄⁻ |
| 273 | unsaturated | F | H | >C(H)(OH) | α-CH₃ | H | —CH₂— | 4-substituted pyridinium, N—C₈H₁₇, I⁻ |
| 274 | unsaturated | F | H | >C(H)(OH) | α-CH₃ | H | —CH₂— | 2-methylpyridine N-oxide |
| 275 | saturated | H | H | >C=O | H | OH | —CH₂— | pyridine N-oxide |
| 276 | saturated | H | F | >C(H)(OH) | H | OH | —CH₂— | N-methylpyridinium CH₃SO₄⁻ |
| 277 | unsaturated | Cl | H | >C=O | H | OH | —CH₂— | pyridine N-oxide |
| 278 | unsaturated | F | F | >C(H)(OH) | α-CH₃ | OH | —CH₂— | 4-substituted pyridinium, N—C₈H₁₇, I⁻ |

-continued

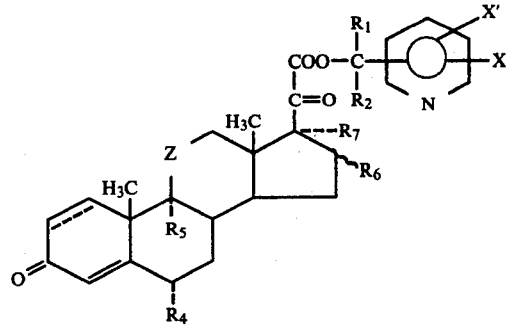

(Ia)

| Example Number | Δ¹ | $R_4$ | $R_5$ | Z | $R_6$ | $R_7$ | $-\overset{R_1}{\underset{R_2}{C}}-$ | pyridine group |
|---|---|---|---|---|---|---|---|---|
| 279 | unsaturated | F | H | >CH–OH | H | OH | $-CH_2-$ | 4-pyridyl |
| 280 | unsaturated | H | H | >C=O | β-$CH_3$ | OH | $-CH_2-$ | 2-methyl-N-methylpyridinium $CH_3SO_4^-$ |
| 281 | unsaturated | $CH_3$ | H | >CH–OH | H | OH | $-CH_2-$ | 2,6-dimethylpyridyl (shown as N, $CH_3$) |
| 282 | unsaturated | F | H | >CH–OH | α-$CH_3$ | OH | $-CH_2-$ | pyridyl · HCl |
| 283 | unsaturated | H | H | >C=O | H | OH | $-CH_2-$ | 4-(N-octyl)pyridinium $I^-$ (+N–$C_8H_{17}$) |
| 284 | saturated | F | H | >CH–OH | $-O-C(CH_3)_2-O-$ |  | $-CH_2-$ | pyridine N-oxide (N→O) |
| 285 | unsaturated | H | F | >CH–OH | $-O-C(C_2H_5)_2-O-$ |  | $-CH_2-$ | 3-pyridyl |
| 286 | unsaturated | H | F | >CH–OH | $-O-C(CH_3)(C_6H_5)-O-$ |  | $-CH_2-$ | 2-methyl-N-methylpyridinium $CH_3SO_4^-$ |
| 287 | unsaturated | F | Cl | >CH–OH | α-$CH_3$ | H | $-CH_2-$ | 4-pyridyl |

-continued

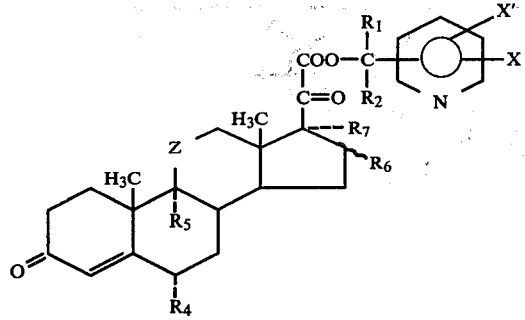

| Example Number | Δ¹ | $R_4$ | $R_5$ | Z | $R_6$ | $R_7$ | $\begin{matrix}R_1\\-C-\\R_2\end{matrix}$ | pyridyl group |
|---|---|---|---|---|---|---|---|---|
| 288 | unsaturated | H | H | >C(H)(OH) | —O—C(CH₃)(CH₃)—O— | | —CH₂— | 2-methylpyridine N-oxide |
| 289 | unsaturated | H | F | >C(H)(OH) | α-CH₃ | H | —CH₂— | 2-pyridyl |
| 290 | unsaturated | F | F | >C(H)(OH) | H | OCOC₃H₇ | —CH₂— | 4-pyridyl |
| 291 | unsaturated | F | H | >C(H)(OH) | —O—C(CH₃)(CH₃)—O— | | —CH₂— | 4-pyridyl·HCl |
| 292 | unsaturated | F | F | >C(H)(OH) | —O—C(CH₃)(CH₃)—O— | | —CH₂— | 2-methyl-N-octylpyridinium I⁻ |
| 293 | saturated | H | H | >C=O | H | OH | —CH₂— | 2-pyridyl·HCl |
| 294 | saturated | H | F | >C(H)(OH) | H | OCO—C₆H₅ | —CH₂— | N-methylpyridinium CH₃SO₄⁻ |
| 295 | unsaturated | Cl | H | >C=O | H | OCOC₃H₇ | —CH₂— | 4-pyridyl |
| 296 | unsaturated | F | F | >C(H)(OH) | α-CH₃ | OCOC₂H₅ | —CH₂— | pyridine N-oxide |

-continued (Ia)

[Structure of steroid compound with R groups and pyridine substituent shown]

| Example Number | Δ¹ | R₄ | R₅ | Z | R₆ | R₇ | $-\underset{R_2}{\overset{R_1}{\underset{|}{\overset{|}{C}}}}-$ | pyridine group |
|---|---|---|---|---|---|---|---|---|
| 297 | unsaturated | F | H | >C<H,OH | H | OCOCH₃ | —CH₂— | N-methylpyridinium CH₃SO₄⁻ |
| 298 | unsaturated | H | H | >C=O | β-CH₃ | OCOC₃H₇ | —CH₂— | pyridine |
| 299 | unsaturated | CH₃ | H | >C<H,OH | H | OCO—Ph | —CH₂— | pyridine N-oxide |
| 300 | unsaturated | F | H | >C<H,OH | α-CH₃ | OCOCH₃ | —CH₂— | N-octylpyridinium I⁻ |
| 301 | unsaturated | H | H | >C<H,OH | H | OCO—Ph | —CH₂— | pyridine·HCl |

$$R-COO-\underset{R_2}{\overset{R_1}{\underset{|}{\overset{|}{C}}}}-\underset{N}{\text{pyridine}}-X,X' \quad (I)$$

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of the equivalence of the following claims.

What is claimed is:

1. A compound selected from the group consisting of:
(a) compounds having the structural formula wherein $R_1$ and $R_2$, which can be the same or different, are each hydrogen, $C_1$-$C_5$ alkyl, $C_1$-$C_5$ alkoxy, $C_1$-$C_5$ alkylthio, phenyl, or substituted phenyl having one or more substituents each of which is selected from the group consisting of $C_1$-$C_5$ alkyl, $C_1$-$C_5$ alkoxy, chloro and dialkylamino wherein the alkyl portions, which can be the same or different, each have 1 to 5 carbon atoms, with the proviso that when $R_1$ is alkoxy or alkylthio, then $R_2$ cannot be alkoxy or alkylthio; X and X', which can be the same or different, are each hydrogen, $C_1$-$C_5$ alkyl, carboxy, $C_2$-$C_6$ alkoxycarbonyl, halo, $C_1$-$C_5$ alkoxy, dialkylcarbamyl wherein the alkyl portions, which can be the same or different, each have 1 to 5 carbon atoms, phenyl, or substituted phenyl having one or more substituents each of which is selected from the group consisting of $C_1$–$C_5$ alkyl, $C_1$–$C_5$ alkoxy, $C_1$–$C_6$ alkanoyl, $C_1$–$C_6$ alkanoyloxy, halo, cyano, $C_2$–$C_6$ alkoxycarbonyl, $C_1$–$C_5$ alkylthio, nitro, $C_1$–$C_5$ haloalkyl have one or more halo substituents, carboxy, $C_1$–$C_5$ alkylsulfonyl, dialkylamino wherein the alkyl portions, which can be the same or different, each have 1 to 5 carbon atoms, and dialkylcarbamyl wherein the alkyl portions, which can be the same or different, each have 1 to 5 carbon atoms; the pyridyl ring is oriented such that it is attached to the

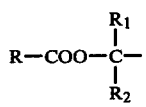

portion of the molecule via a carbon-carbon bond; and R—COO— is the acyloxy residue of:
(1) a monocarboxylic acid selected from the group consisting of indomethacin, aspirin, naproxen, sulindac, tolmetin, diflunisal, flurbiprofen, indoprofen, fenclozic acid, ketoprofen, alclofenac, bucloxic acid, cinchophen, pirprofen, fluprofen, flutiazin, clometacin, flufenisal, salsalate, ibuprofen, ibufenac, cinmetacin, furobufen and prodolic acid;
(2) a steroidal monocarboxylic acid having the structural formula

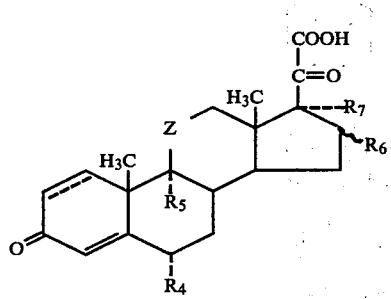

wherein $R_4$ is hydrogen, fluoro, chloro, or methyl; $R_5$ is hydrogen, fluoro or chloro; $R_6$ is hydrogen, methyl, hydroxy or —$OCOR_8$ wherein $R_8$ is $C_1$–$C_7$ straight or branched alkyl or phenyl; $R_7$ is hydrogen, hydroxy, or —O-$COR_8$ wherein $R_8$ is as defined above, with the proviso that when $R_6$ is hydroxy or —$OCOR_8$ and $R_7$ is other than hydrogen, then $R_6$ and $R_7$ are identical; or $R_6$ and $R_7$ are combined to form a divalent radical of the type

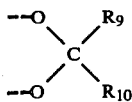

wherein $R_9$ and $R_{10}$, which can be the same or different, are each $C_1$–$C_7$ straight or branched alkyl or phenyl; Z is carbonyl or β-hydroxymethylene; the wavy line at the 16-position indicates the α or β-configuration; and the dotted line in ring A indicates that the 1,2-linkage is saturated or unsaturated;
(3) a cephalosporin antibiotic having one carboxylic acid function;
(4) a penicillin antibiotic having one carboxylic acid function; or
(5) a monocarboxylic acid selected from the group consisting of γ-aminobutyric acid, captopril and valproic acid;
(b) compounds having the structural formula

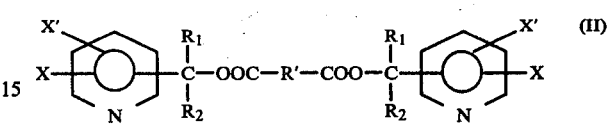

wherein the groups attached to each end of the divalent —OOC—R'—COO— residue are identical to each other; $R_1$, $R_2$, X, X' and the orientation of the pyridyl ring are as defined with respect to formula (I) above; and —OOC—R'—COO— is the di(acyloxy) residue of:
(1) a cephalosporin antibiotic having two carboxylic acid functions;
(2) a penicillin antibiotic having two carboxylic acid functions; or
(3) the dicarboxylic acid, methotrexate; and
(c) the non-toxic pharmaceutically acceptable acid addition salts, quaternary ammonium salts, and N-oxides of the compounds of formulas (I) and (II) above.

2. A compound as defined by claim 1, having the structural formula (I).

3. A compound as defined by claim 1, said compound being a pharmaceutically acceptable acid addition salt of a compound having the structural formula (I).

4. A compound as defined by claim 1, said compound being a hydrochloride salt of a compound having the structural formula (I).

5. A compound as defined by claim 1, said compound being a pharmaceutically acceptable quaternary ammonium salt of a compound having the structural formula (I).

6. A compound as defined by claim 1, said compound being an N-oxide of a compound having the structural formula (I).

7. A compound as defined by claim 1, having the structural formula (II).

8. A compound as defined by claim 1, said compound being a pharmaceutically acceptable acid addition salt of a compound having the structural formula (II).

9. A compound as defined by claim 1, said compound being a hydrochloride salt of a compound having the structural formula (II).

10. A compound as defined by claim 1, said compound being a quaternary ammonium salt of a compound having the structural formula (II).

11. A compound as defined by claim 1, said compound being an N-oxide of a compound having the structural formula (II).

12. A compound as defined by claim 1, wherein one of $R_1$ and $R_2$ is hydrogen.

13. A compound as defined by claim 1, wherein $R_1$ and $R_2$ are each hydrogen.

14. A compound as defined by claim 12, wherein the other of $R_1$ and $R_2$ is methyl.

15. A compound as defined by claim 12, wherein the other of $R_1$ and $R_2$ is phenyl.

16. A compound as defined by claim 12, wherein the other of $R_1$ and $R_2$ is $C_1$-$C_5$ alkyl.

17. A compound as defined by claim 12, wherein the other of $R_1$ and $R_2$ is $C_1$-$C_5$ alkoxy.

18. A compound as defined by claim 12, wherein the other of $R_1$ and $R_2$ is $C_1$-$C_5$ alkylthio.

19. A compound as defined by claim 12, wherein the other of $R_1$ and $R_2$ is substituted phenyl.

20. A compound as defined by claim 1, wherein one of X and X' is hydrogen.

21. A compound as defined by claim 1, wherein X and X' are each hydrogen.

22. A compound as defined by claim 20, wherein the other of X and X' is methyl.

23. A compound as defined by claim 1, wherein X and X' are each methyl.

24. A compound as defined by claim 20, wherein the other of X and X' is $C_1$-$C_5$ alkyl.

25. A compound as defined by claim 20, wherein the other of X and X' is carboxy.

26. A compound as defined by claim 20, wherein the other of X and X' is $C_2$-$C_6$ alkoxycarbonyl.

27. A compound as defined by claim 20, wherein the other of X and X' is halo.

28. A compound as defined by claim 20, wherein the other of X and X' is $C_1$-$C_5$ alkoxy.

29. A compound as defined by claim 20, wherein the other of X and X' is dialkylcarbamyl.

30. A compound as defined by claim 20, wherein the other of X and X' is phenyl.

31. A compound as defined by claim 20, wherein the other of X and X' is substituted phenyl.

32. A compound as defined by claim 1, wherein the

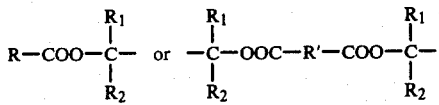

grouping is located ortho to the pyridyl nitrogen atom.

33. A compound as defined by claim 1, wherein the

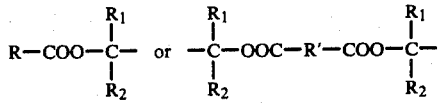

grouping is located para to the pyridyl nitrogen atom.

34. A compound as defined by claim 1, wherein R—COO— is the acyloxy residue of a monocarboxylic acid selected from the group consisting of indomethacin, aspirin, naproxen, sulindac, ibuprofen, tolmetin, diflunisal, flurbiprofen, indoprofen, fenclozic acid, ketoprofen, alclofenac, bucloxic acid, cinchophen, cinmetacin, ibufenac, furoburen, prodolic acid, pirprofen, fluprofen, flutiazin, clometacin, flufenisal and salsalate.

35. A compound as defined by claim 34, wherein R—COO— is the acyloxy residue of indomethacin.

36. A compound as defined by claim 34, wherein R—COO— is the acyloxy residue of aspirin.

37. A compound as defined by claim 34, wherein R—COO— is the acyloxy of naproxen.

38. A compound as defined by claim 34, wherein R—COO— is the acyloxy residue of sulindac.

39. A compound as defined by claim 34, wherein R—COO— is the acyloxy residue of ibuprofen.

40. A compound as defined by claim 34, wherein R—COO— is the acyloxy residue of diflunisal.

41. A compound as defined by claim 34, wherein R—COO— is the acyloxy residue of tolmetin.

42. A compound as defined by claim 34, wherein R—COO— is the acyloxy residue of flurbiprofen.

43. A compound as defined by claim 34, wherein R—COO— is the acyloxy residue of indoprofen.

44. A compound as defined by claim 34, wherein R—COO— is the acyloxy residue of fenclozic acid.

45. A compound as defined by claim 34, wherein R—COO— is the acyloxy residue of ketoprofen.

46. A compound as defined by claim 34, wherein R—COO— is the acyloxy residue of alclofenac.

47. A compound as defined by claim 34, wherein R—COO— is the acyloxy residue of bucloxic acid.

48. A compound as defined by claim 34, wherein R—COO— is the acyloxy residue of cinchophen.

49. A compound as defined by claim 34, wherein R—COO— is the acyloxy residue of cinmetacin.

50. A compound as defined by claim 34, wherein R—COO— is the acyloxy residue of ibufenac.

51. A compound as defined by claim 34, wherein R—COO— is the acyloxy residue of furobufen.

52. A compound as defined by claim 34, wherein R—COO— is the acyloxy residue of prodolic acid.

53. A compound as defined by claim 34, wherein R—COO— is the acyloxy residue of pirprofen.

54. A compound as defined by claim 34, wherein R—COO— is the acyloxy residue of fluprofen.

55. A compound as defined by claim 34, wherein R—COO— is the acyloxy residue of flutiazin.

56. A compound as defined by claim 34, wherein R—COO— is the acyloxy residue of clometacin.

57. A compound as defined by claim 34, wherein R—COO— is the acyloxy residue of flufenisal.

58. A compound as defined by claim 34, wherein R—COO— is the acyloxy residue of salsalate.

59. A compound as defined by claim 1, wherein R—COO— is the acyloxy residue of a cephalosporin antibiotic containing one carboxylic acid function.

60. A compound as defined by claim 59, wherein R—COO— is the acyloxy residue of a compound selected from the group consisting of cefmetazole, cefazolin, cephalexin, cefoxitin, cephacetrile, cephaloglycin, cephaloridine, cephalothin, cephapirin and cephradine.

61. A compound as defined by claim 59, wherein R—COO— is the acyloxy residue of cefmetazole.

62. A compound as defined by claim 59, wherein R—COO— is the acyloxy residue of cefazolin.

63. A compound as defined by claim 59, wherein R—COO— is the acyloxy residue of cephalexin.

64. A compound as defined by claim 59, wherein R—COO— is the acyloxy residue of cefoxitin.

65. A compound as defined by claim 59, wherein R—COO— is the acyloxy residue of cephacetrile.

66. A compound as defined by claim 59, wherein R—COO— is the acyloxy residue of cephaloglycin.

67. A compound as defined by claim 59, wherein R—COO— is the acyloxy residue of cephaloridine.

68. A compound as defined by claim 59, wherein R—COO— is the acyloxy residue of cephalothin.

69. A compound as defined by claim 59, wherein R—COO— is the acyloxy residue of cephapirin.

70. A compound as defined by claim 59, wherein R—COO— is the acyloxy residue of cephradine.

71. A compound as defined by claim 1, wherein R—COO— is the acyloxy residue of a penicillin antibiotic containing one carboxylic acid function.

72. A compound as defined by claim 71, wherein R—COO— is the acyloxy residue of a compound selected from the group consisting of ampicillin, amoxicillin, hetacillin, carfecillin, carindacillin, amylpenicillin, azidocillin, benzylpenicillinic acid, clometacillin, cloxacillin, cyclacillin, methicillin, nafcillin, 2-pentenylpenicillin, penicillin BT, penicillin O, penicillin S, penicillin V, chlorobutin penicillin, dicloxacillin, diphenicillin, heptylpenicillin and metampicillin.

73. A compound as defined by claim 71, wherein R—COO— is the acyloxy residue of ampicillin.

74. A compound as defined by claim 71, wherein R—COO— is the acyloxy residue of penicillin V.

75. A compound as defined by claim 71, wherein R—COO— is the acyloxy residue of amoxicillin.

76. A compound as defined by claim 71, wherein R—COO— is the acyloxy residue of hetacillin.

77. A compound as defined by claim 71, wherein R—COO— is the acyloxy residue of benzylpenicillinic acid.

78. A compound as defined by claim 71, wherein R—COO— is the acyloxy residue of cloxacillin.

79. A compound as defined by claim 71, wherein R—COO— is the acyloxy residue of dicloxacillin.

80. A compound as defined by claim 71, wherein R—COO— is the acyloxy residue of methicillin.

81. A compound as defined by claim 71, wherein R—COO— is the acyloxy residue of nafcillin.

82. A compound as defined by claim 1, wherein R—COO— is the acyloxy residue of γ-aminobutyric acid.

83. A compound as defined by claim 1, wherein R—COO— is the acyloxy residue of captopril.

84. A compound as defined by claim 1, wherein R—COO— is the acyloxy residue of valproic acid.

85. A compound as defined by claim 1, wherein R—COO— is the acyloxy residue of a steroidal monocarboxylic acid having the structural formula (III)

[Structural formula of steroid with COOH, C=O, H3C, Z, H3C, R7, R6, R5, R4 substituents]

wherein $R_4$ is hydrogen, fluoro, chloro, or methyl; $R_5$ is hydrogen, fluoro or chloro; $R_6$ is hydrogen, methyl, hydroxy or —OCOR$_8$ wherein $R_8$ is $C_1$-$C_7$ straight or branched alkyl or phenyl; $R_7$ is hydrogen, hydroxy, or —OCOR$_8$ wherein $R_8$ is as defined above, with the proviso that when $R_6$ is hydroxy or —OCOR$_8$ and $R_7$ is other than hydrogen, then $R_6$ and $R_7$ are identical; or $R_6$ and $R_7$ are combined to form a divalent radical of the type $$\begin{array}{c} -O \\ -O \end{array} \diagdown C \diagup \begin{array}{c} R_9 \\ R_{10} \end{array}$$

wherein $R_9$ and $R_{10}$, which can be the same or different, are each $C_1$-$C_7$ straight or branched alkyl or phenyl; Z is carbonyl or β-hydroxymethylene; the wavy line at the 16-position indicates the α or β-configuration; and the dotted line in ring A indicates that the 1,2-linkage is saturated or unsaturated.

86. A compound as defined by claim 85, wherein the structural variables represented by $R_4$, $R_5$, $R_6$, $R_7$, Z and the dotted and wavy lines are identical to those of a known antiinflammatory steroid selected from the group consisting of hydrocortisone, betamethasone, dexamethasone, prednisolone, triamcinolone, fluocortolone, cortisone, fludrocortisone, chloroprednisone, flumethasone, fluprednisolone, meprednisone, methyl prednisolone, paramethasone, prednisone, flurandrenolone acetonide, amicinafal, amcinafide, clocortolone, desonide, desoximetasone, difluprednate, flunisolide, fluocinolone acetonide, triamcinolone acetonide, betamethasone 17-benzoate and betamethasone 17-valerate.

87. A compound as defined by claim 85, wherein the structural variables represented by $R_4$, $R_5$, $R_6$, Z and the dotted and wavy lines are identical to those of a known anti-inflammatory steroid selected from the group consisting of hydrocortisone, cortisone, fludrocortisone, betamethasone, chloroprednisone, dexamethasone, flumethasone, fluprednisolone, meprednisone, methyl prednisolone, paramethasone and prednisone, and $R_7$ is —OCOR$_8$ wherein $R_8$ is defined as in claim 85.

88. A compound as defined by claim 87, wherein $R_8$ is $CH_3$, $C_2H_5$, $C_3H_7$ or phenyl.

89. A compound as defined by claim 85, wherein the structural variables represented by $R_4$, $R_5$, Z and the wavy and dotted lines are identical to those of triamcinolone, and $R_6$ and $R_7$ are identical —OCOR$_8$ groupings wherein $R_8$ is $C_1$-$C_7$ straight or branched alkyl or phenyl.

90. A compound as defined by claim 85, wherein R—COO— is the acyloxy residue of 6α-fluoro-11β-hydroxy-16α-methyl-3,20-dioxopregna-1,4-dien-21-oic acid.

91. A compound as defined by claim 85, wherein R—COO— is the acyloxy residue of 9α-fluoro-11β,17α-dihydroxy-16β-methyl-3,20-dioxopregna-1,4-dien-21-oic acid or a 17-ester thereof.

92. A compound as defined by claim 85, wherein R—COO— is the acyloxy residue of 9α-fluoro-11β,17α-dihydroxy-16α-methyl-3,20-dioxopregna-1,4-dien-21-oic acid or a 17-ester thereof.

93. A compound as defined by claim 85, wherein R—COO— is the acyloxy residue of 11β,17α-dihydroxy-3,20-dioxopregna-4-en-21-oic acid or a 17-ester thereof.

94. A compound as defined by claim 85, wherein R—COO— is the acyloxy residue of 9-α-fluoro-11β,16α,17α-trihydroxy-3,20-dioxopregna-1,4-dien-21-oic acid or a 17-ester thereof.

95. A compound as defined by claim 85, wherein R—COO— is the acyloxy residue of 11β,17α-dihydroxy-3,20-dioxopregna-1,4-dien-21-oic acid or a 17-ester thereof.

96. A compound as defined by claim 85, wherein R—COO— is the acyloxy residue of 9α-fluoro-11β,7α-dihydroxy-16β-methyl-3,20-dioxopregna-1,4-dien-21-oic acid.

97. A compound as defined by claim 85, wherein R—COO— is the acyloxy residue of 9α-fluoro-11β,17α-dihydroxy-16α-methyl-3,20-dioxopregna-1,4-dien-21-oic acid.

98. A compound as defined by claim 85, wherein R—COO— is the acyloxy residue of 11β,17α-dihydroxy-3,20-dioxopregna-4-en-21-oic acid.

99. A compound as defined by claim 85, wherein R—COO— is the acyloxy residue of 9α-fluoro-11β,16α,17α-trihydroxy-3,20-dioxopregna-1,4-dien-21-oic acid.

100. A compound as defined by claim 85, wherein R—COO— is the acyloxy residue of 11β,17α-dihydroxy-3,20-dioxopregna-1,4-dien-21-oic acid.

101. A compound as defined by claim 1, wherein —OOC—R'—COO— is the di(acyloxy) residue of a cephalosporin antibiotic having two carboxylic acid functions.

102. A compound as defined by claim 101, wherein —OOC—R'—COO— is the di(acyloxy) residue of cephalosporin C.

103. A compound as defined by claim 101, wherein —OOC—R'—COO— is the di(acyloxy) residue of cephamycin A.

104. A compound as defined by claim 101, wherein —OOC—R'—COO— is the di(acyloxy) residue of cephamycin B.

105. A compound as defined by claim 101, wherein —OOC—R'—COO— is the di(acyloxy) residue of cephamycin C.

106. A compound as defined by claim 1, wherein —OOC—R'—COO— is the di(acyloxy) residue of a penicillin antibiotic having two carboxylic acid functions.

107. A compound as defined by claim 106, wherein —OOC—R'—COO— is the di(acyloxy) residue of carbenicillin.

108. A compound as defined by claim 106, wherein —OOC—R'—COO— is the di(acyloxy) residue of penicillin N.

109. A compound as defined by claim 1, wherein —OOC—R'—COO— is the di(acyloxy) residue of methotrexate.

110. A pharmaceutical composition of matter comprising an anti-inflammatory, analgesic, or antipyretic effective amount of a compound as defined by claim 34, and a pharmaceutically acceptable carrier therefor.

111. A method of eliciting an anti-inflammatory, analgesic or antipyretic response in a warm-blooded animal, which comprises administering to such animal an anti-inflammatory, analgesic or antipyretic effective amount of a compound as defined by claim 34.

112. A pharmaceutical composition of matter comprising an antibiotic effective amount of a compound as defined by claim 59, and a pharmaceutically acceptable carrier therefor.

113. A method of eliciting an antibiotic response in a warm-blooded animal, which comprises administering to such animal an antibiotic effective amount of a compound as defined by claim 59.

114. A pharmaceutical composition of matter comprising an antibiotic effective amount of a compound as defined by claim 71, and a pharmaceutically acceptable carrier therefor.

115. A method of eliciting an antibiotic response in a warm-blooded animal, which comprises administering to such animal an antibiotic effective amount of a compound as defined by claim 71.

116. A pharmaceutical composition of matter comprising an anticonvulsant effect amount of a compound as defined by claim 82, and a pharmaceutically acceptable carrier therefor.

117. A method of treating or preventing convulsions in a warm-blooded animal, which comprises administering to such animal an anticonvulsant effective amount of a compound as defined by claim 82.

118. A pharmaceutical composition of matter comprising an antihypertensive effective amount of a compound as defined by claim 83, and a pharmaceutically acceptable carrier therefor.

119. A method of treating or preventing hypertension in a warm-blooded animal, which comprises administering to such animal an antihypertensive effective amount of a compound as defined by claim 83.

120. A pharmaceutical composition of matter comprising an anticonvulsant or antiepileptic effective amount of a compound as defined by claim 84, and a pharmaceutically acceptable carrier therefor.

121. A method of treating or preventing convulsions or epilepsy in a warm-blooded animal, which comprises administering to such animal an anticonvulsant or antiepileptic effective amount of a compound as defined by claim 84.

122. A pharmaceutical composition of matter comprising an anti-inflammatory effective amount of a compound as defined by claim 85, and a pharmaceutically acceptable carrier therefor.

123. A method of eliciting an anti-inflammatory response in a warm-blooded animal, which comprises administering to such animal an anti-inflammatory effective amount of a compound as defined by claim 85.

124. A pharmaceutical composition of matter comprising an antibiotic effective amount of a compound as defined by claim 101, and a pharmaceutically acceptable carrier therefor.

125. A method of eliciting an antibiotic response in a warm-blooded animal, which comprises administering to such animal an antibiotic effective amount of a compound as defined by claim 101.

126. A pharmaceutical composition of matter comprising an antibiotic effective amount of a compound as defined by claim 106, and a pharmaceutically acceptable carrier therefor.

127. A method of eliciting an antibiotic response in a warm-blooded animal, which comprises administering to such animal an antibiotic effective amount of a compound as defined by claim 106.

128. A pharmaceutical composition of matter comprising an antineoplastic effective amount of a compound as defined by claim 109, and a pharmaceutically acceptable carrier therefor.

129. A method of eliciting an antineoplastic response in a warm-blooded animal, which comprises administering to such animal an antineoplastic effective amount of a compound as defined by claim 109.

* * * * *